(12) United States Patent
Solomon et al.

(10) Patent No.: US 8,343,112 B2
(45) Date of Patent: Jan. 1, 2013

(54) DISINFECTING CAPS HAVING AN EXTENDABLE FEATURE AND RELATED SYSTEMS AND METHODS

(75) Inventors: Donald D. Solomon, North Salt Lake, UT (US); F. Mark Ferguson, Salt Lake City, UT (US); Steven Bandis, West Jordan, UT (US); James Mercer, West Jordan, UT (US); Michael Howlett, Salt Lake City, UT (US); Robert Hitchcock, Sandy, UT (US)

(73) Assignees: Catheter Connections, Inc., Salt Lake City, UT (US); The University of Utah Research Foundation, Salt Lake City, UT (US)

( * ) Notice: Subject to any disclaimer, the term of this patent is extended or adjusted under 35 U.S.C. 154(b) by 153 days.

(21) Appl. No.: 12/956,704

(22) Filed: Nov. 30, 2010

(65) Prior Publication Data
US 2011/0217212 A1   Sep. 8, 2011

Related U.S. Application Data

(63) Continuation-in-part of application No. 12/917,336, filed on Nov. 1, 2010, which is a continuation-in-part of application No. 12/610,141, filed on Oct. 30, 2009, now Pat. No. 8,172,825.

(60) Provisional application No. 61/265,207, filed on Nov. 30, 2009.

(51) Int. Cl.
*A61M 5/14* (2006.01)
*B65D 43/03* (2006.01)
*A61L 2/00* (2006.01)
*A61L 2/18* (2006.01)
*A61L 9/00* (2006.01)

(52) U.S. Cl. ......... 604/256; 604/905; 220/380; 422/292

(58) Field of Classification Search .................. 604/905, 604/29, 283, 256, 403, 533; 424/292, 28; 220/380
See application file for complete search history.

(56) References Cited

U.S. PATENT DOCUMENTS

| 2,351,804 A | 6/1944 | Jerome |
| 3,446,596 A | 5/1969 | Salivar et al. |
| 3,987,930 A | 10/1976 | Fuson |

(Continued)

FOREIGN PATENT DOCUMENTS

| WO | WO-2006/099306 | 9/2006 |

(Continued)

OTHER PUBLICATIONS

Curos Port Protector web page from http://www.iveramed.com./, dated Jul. 11, 2008.

(Continued)

*Primary Examiner* — Kevin C Sirmons
*Assistant Examiner* — William Carpenter
(74) *Attorney, Agent, or Firm* — Sunstein Kann Murphy & Timbers LLP

(57) ABSTRACT

Some assemblies can include a male cap and a female cap, each of which can be used to cover separated medical connectors. In certain arrangements, a male cap can include a movable carriage that transitions from a retracted position when an assembly with which the male cap is associated is in a closed state to an extended position when the assembly is in an open state.

34 Claims, 25 Drawing Sheets

U.S. PATENT DOCUMENTS

| | | | |
|---|---|---|---|
| 4,232,677 A | 11/1980 | Leibinsohn | |
| 4,324,239 A | 4/1982 | Gordon et al. | |
| 4,340,052 A | 7/1982 | Dennehey et al. | |
| 4,346,703 A | 8/1982 | Dennehey et al. | |
| 4,354,490 A | 10/1982 | Rogers | |
| 4,369,781 A | 1/1983 | Gilson et al. | |
| 4,402,691 A | 9/1983 | Rosenthal et al. | |
| 4,432,764 A | 2/1984 | Lopez | |
| 4,432,766 A | 2/1984 | Bellotti et al. | |
| 4,440,207 A | 4/1984 | Genatempo et al. | |
| 4,450,624 A | 5/1984 | Collier | |
| 4,778,447 A | 10/1988 | Velde et al. | |
| 4,838,875 A | 6/1989 | Somor | |
| 5,205,821 A | 4/1993 | Kruger et al. | |
| 5,242,425 A | 9/1993 | White et al. | |
| 5,439,451 A * | 8/1995 | Collinson et al. | 604/247 |
| 5,466,219 A | 11/1995 | Lynn et al. | |
| 5,492,147 A * | 2/1996 | Challender et al. | 137/614.05 |
| 5,536,258 A * | 7/1996 | Folden | 604/265 |
| 5,554,135 A | 9/1996 | Menyhay | |
| 5,694,978 A | 12/1997 | Heilmann et al. | |
| 5,738,663 A * | 4/1998 | Lopez | 604/249 |
| 5,792,120 A | 8/1998 | Menyhay | |
| 5,894,015 A | 4/1999 | Rechtin | |
| 5,951,519 A | 9/1999 | Utterberg | |
| 6,045,539 A | 4/2000 | Menyhay | |
| 6,171,287 B1 | 1/2001 | Lynn et al. | |
| 6,932,795 B2 * | 8/2005 | Lopez et al. | 604/249 |
| 6,960,191 B2 | 11/2005 | Howlett et al. | |
| 7,014,169 B2 * | 3/2006 | Newton et al. | 251/149.6 |
| 7,040,598 B2 | 5/2006 | Raybuck | |
| 7,198,611 B2 | 4/2007 | Connell et al. | |
| D547,446 S | 7/2007 | Racz et al. | |
| D550,355 S | 9/2007 | Racz et al. | |
| 7,316,669 B2 | 1/2008 | Ranalletta | |
| D607,325 S | 1/2010 | Rogers et al. | |
| 7,762,524 B2 * | 7/2010 | Cawthon et al. | 251/149.6 |
| 7,780,794 B2 | 8/2010 | Rogers et al. | |
| 7,922,701 B2 * | 4/2011 | Buchman | 604/256 |
| 7,985,302 B2 | 7/2011 | Rogers et al. | |
| 2002/0093192 A1 | 7/2002 | Matkovich | |
| 2003/0140441 A1 | 7/2003 | Stafford | |
| 2003/0153865 A1 | 8/2003 | Connell et al. | |
| 2003/0198502 A1 | 10/2003 | Maloney et al. | |
| 2004/0201216 A1 | 10/2004 | Segal et al. | |
| 2004/0214316 A1 | 10/2004 | O'Connell | |
| 2005/0033267 A1 | 2/2005 | Decaria | |
| 2005/0038397 A1* | 2/2005 | Newton et al. | 604/249 |
| 2005/0124970 A1 | 6/2005 | Kunin et al. | |
| 2005/0203460 A1 | 9/2005 | Kim | |
| 2005/0245883 A1 | 11/2005 | Baldwin | |
| 2005/0266714 A1 | 12/2005 | Higgins et al. | |
| 2006/0030827 A1 | 2/2006 | Raulerson et al. | |
| 2007/0112333 A1 | 5/2007 | Hoang et al. | |
| 2007/0202177 A1 | 8/2007 | Hoang | |
| 2007/0287989 A1 | 12/2007 | Crawford et al. | |
| 2007/0293818 A1 | 12/2007 | Stout et al. | |
| 2007/0293822 A1 | 12/2007 | Crawford et al. | |
| 2008/0021381 A1 | 1/2008 | Lurvey et al. | |
| 2008/0027399 A1 | 1/2008 | Harding et al. | |
| 2008/0038167 A1 | 2/2008 | Lynn | |
| 2008/0039803 A1 | 2/2008 | Lynn | |
| 2008/0086091 A1 | 4/2008 | Anderson et al. | |
| 2008/0095680 A1 | 4/2008 | Steffens et al. | |
| 2008/0105704 A1 | 5/2008 | Pritchard | |
| 2008/0107564 A1 | 5/2008 | Sternberg et al. | |
| 2008/0132880 A1* | 6/2008 | Buchman | 604/533 |
| 2008/0147047 A1 | 6/2008 | Davis et al. | |
| 2008/0177250 A1 | 7/2008 | Howlett et al. | |
| 2008/0190485 A1* | 8/2008 | Guala | 137/1 |
| 2008/0235888 A1 | 10/2008 | Vaillancourt et al. | |
| 2009/0008393 A1 | 1/2009 | Howlett et al. | |
| 2009/0062766 A1 | 3/2009 | Howlett et al. | |
| 2009/0205151 A1 | 8/2009 | Fisher et al. | |
| 2010/0047123 A1 | 2/2010 | Solomon et al. | |
| 2010/0049170 A1 | 2/2010 | Solomon et al. | |
| 2010/0063482 A1* | 3/2010 | Mansour et al. | 604/539 |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | |
| 2011/0213341 A1 | 9/2011 | Solomon et al. | |

FOREIGN PATENT DOCUMENTS

| | | |
|---|---|---|
| WO | WO-2008/089196 | 7/2008 |
| WO | WO-2008/100950 | 8/2008 |
| WO | WO-2010/002808 | 1/2010 |
| WO | WO-2010/141508 | 12/2010 |
| WO | WO-2011/053924 | 5/2011 |
| WO | WO-2011/066565 | 6/2011 |
| WO | WO-2011/066586 | 6/2011 |

OTHER PUBLICATIONS

Curos Port Protector product brochure, circa Nov. 2008, http://www.iveramed.com/docs/Curos%20Brochure-FINAL.pdf.

Hospira Male/Female Sterile Cap product packaging insert and brochure, circa Aug. 2004.

BD Q-Syte Luer Access Split Septum product brochure, circa Nov. 2008, http://www.bd.com/infusion/pdfs/D16333.pdf.

Tego Connector product brochure, circa Nov. 2008, http://www.icumed.com/Docs-Tego/M1-1148%20TEGO%20Folder%20Brochure%20Rev.3.pdf.

Baxa Corporation Launches PadLock Set Saver for IV Safety press release, Oct. 10, 2007, http://www.pr.com/press-release/555432.

Baxa Corporation PadLock Set Saver Specifications and Instructions for Use, Copyright 2007, http://www.baxa.com/resources/docs/5300103905C.pdf.

Baxa Corporation Padlock product brochure, Copyright 2007, http://www.baxa.com/resources/docs/5300104405A.pdf.

Baxa Corporation Padlock Microbial Testing Technical Paper, Copyright 2007, http://www.baxa.com/resources/docs/technicalPaper/PadlockMicrobialChallengeTechPaper.pdf.

Baxa Corporation Padlock catalog page, Copyright 2009, http://www.baxa.com/SearchResults/ProductDetail/?id=6452BFB9-3048-7B87-701697FB93902BA6.

One Less Problem, Managing Infection Control, Jun. 2008, http://www.baxa.com/resources/docs/OneLessProbPaper.pdf.

Unomedical Medical Products catalog, circa Jan. 2006, http://www.unomedical.net/au/section05/section10/LocalSSI/..%5C..%5Cpdf%5Cmedical.pdf.

Braum product catalog, circa Aug. 2008.

Buchman, et al., "A New Central Venous Catheter Cap: Decreased Microbial Growth and Risk for Catheter-Related Bloodstream Infection," The Journal of Vascular Access 2009, 10: pp. 11-21.

Restriction Requirement mailed Nov. 13, 2008 in U.S. Appl. No. 12/014,388, now abandoned.

Amendment and Response to Restriction Requirement filed Mar. 24, 2009 in U.S. Appl. No. 12/014,388, now abandoned.

Interview Summary mailed Sep. 1, 2009 in U.S. Appl. No. 12/014,388, now abandoned.

Office Action mailed May 5, 2009 in U.S. Appl. No. 12/014,388, now abandoned.

Amendment and Response to Office Action filed Sep. 4, 2009 in U.S. Appl. No. 12/014,388, now abandoned.

Notice of Non-Compliance Amendment mailed Sep. 28, 2009 in U.S. Appl. No. 12/014,388, now abandoned.

Amendment and Response to Office Action filed Oct. 2, 2009 in U.S. Appl. No. 12/014,388, now abandoned.

Final Office Action mailed Jan. 27, 2010 in U.S. Appl. No. 12/014,388, now abandoned.

RCE and Amendment and Response to Office Action filed Apr. 26, 2010 in U.S. Appl. No. 12/014,388, now abandoned.

Office Action mailed Jun. 21, 2010 in U.S. Appl. No. 12/014,388, now abandoned.

Amendment and Response to Office Action filed Oct. 19, 2010 in U.S. Appl. No. 12/014,388, now abandoned.

Interview Summary mailed Oct. 25, 2010 in U.S. Appl. No. 12/014,388, now abandoned.

Final Office Action mailed Dec. 23, 2010 in U.S. Appl. No. 12/014,388, now abandoned.

Express Abandonment filed Feb. 15, 2011 in U.S. Appl. No. 12/014,388, now abandoned.
Restriction Requirement mailed May 21, 2010 in co-pending U.S. Appl. No. 12/164,310, now published as US 2009/0008393.
Amendment and Response to Restriction Requirement filed Jun. 21, 2010 in co-pending U.S. Appl. No. 12/164,310, now published as US 2009/0008393.
Office Action mailed Aug. 16, 2010 in co-pending U.S. Appl. No. 12/164,310, now published as US 2009/0008393.
Amendment and Response to Office Action filed Oct. 29, 2010 in co-pending U.S. Appl. No. 12/164,310, now published as US 2009/0008393.
Interview Summary mailed Oct. 25, 2010 in co-pending U.S. Appl. No. 12/164,310, now published as US 2009/0008393.
Notice of Non-Compliant Amendment mailed Nov. 3, 2010 in co-pending U.S. Appl. No. 12/164,310, now published as US 2009/0008393.
Amendment and Response to Office Action filed Feb. 16, 2011 in co-pending U.S. Appl. No. 12/164,310, now published as US 2009/0008393.
Preliminary Amendment filed Dec. 7, 2010 in co-pending U.S. Appl. No. 12/171,997, now published as US 2009/0062766.
Restriction Requirement mailed Dec. 9, 2010 in co-pending U.S. Appl. No. 12/171,997, now published as US 2009/0062766.
Notification of Transmittal of the International Search Report and the Written Opinion of the International Searching Authority issued Aug. 1, 2008 in International Application No. PCT/US2008/051087.
Notification of Transmittal of the International Search Report and the Written Opinion of the International Searching Authority issued Aug. 31, 2009 in International Application No. PCT/US2009/049094.
Notification of Transmittal of the International Search Report and the Written Opinion of the International Searching Authority issued Jan. 6, 2011 in International Application No. PCT/US2010/054995.
Notification of Transmittal of the International Search Report and the Written Opinion of the International Searching Authority issued Jan. 26, 2011 in International Application No. PCT/US2010/058404.
Notification of Transmittal of the International Search Report and the Written Opinion of the International Searching Authority issued Feb. 7, 2011 in International Application No. PCT/US2010/058453.
Co-pending U.S. Appl. No. 12/917,336 titled Disinfecting Caps and Systems and Associated Methods, filed Nov. 1, 2010.
Co-pending U.S. Appl. No. 29/383,403 titled Capping System for Use With One or More Medical Connectors, filed Jan. 17, 2011.
Co-pending U.S. Appl. No. 12/957,263 titled Disinfecting Caps Having Sealing Features and Related Systems and Methods, filed Nov. 30, 2010.
Maki, Dennis G., "In Vitro Studies of a Novel Antimicrobial Luer-Activated Needleless Connector for Prevention of Catheter-Related Blookstream Infection," Clinical Infection Diseases, Jun. 15, 2010, vol. 50, Issue 12, pp. 1580-1587.
Final Office Action mailed Apr. 22, 2011 in co-pending U.S. Appl. No. 12/164,310, now published as U.S. Publication No. US-2009/0008393.
Response to Requirement for Election of Species filed Apr. 1, 2011 in co-pending U.S. Appl. No. 12/171,997, now published as U.S. Publication No. US-2009/0062766.
Office Action mailed Jun. 9, 2011 in co-pending U.S. Appl. No. 12/171,997, now published as U.S. Publication No. US-2009/0062766.
Preliminary Amendment filed Jun. 13, 2011 in co-pending U.S. Appl. No. 29/383,403.
Preliminary Amendment filed May 13, 2011 in co-pending U.S. Appl. No. 12/957,263.

* cited by examiner

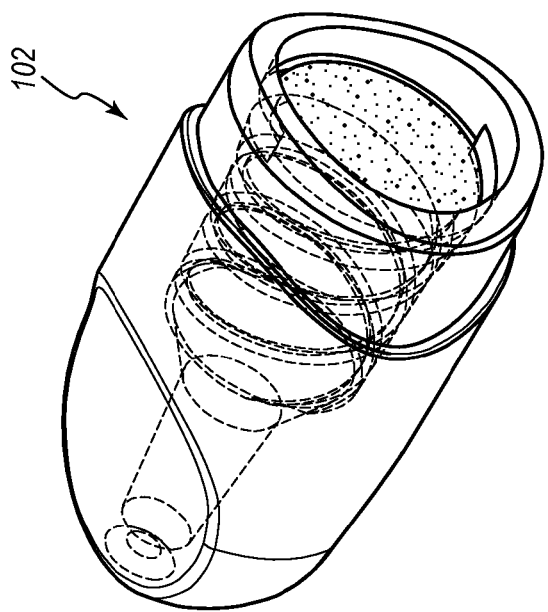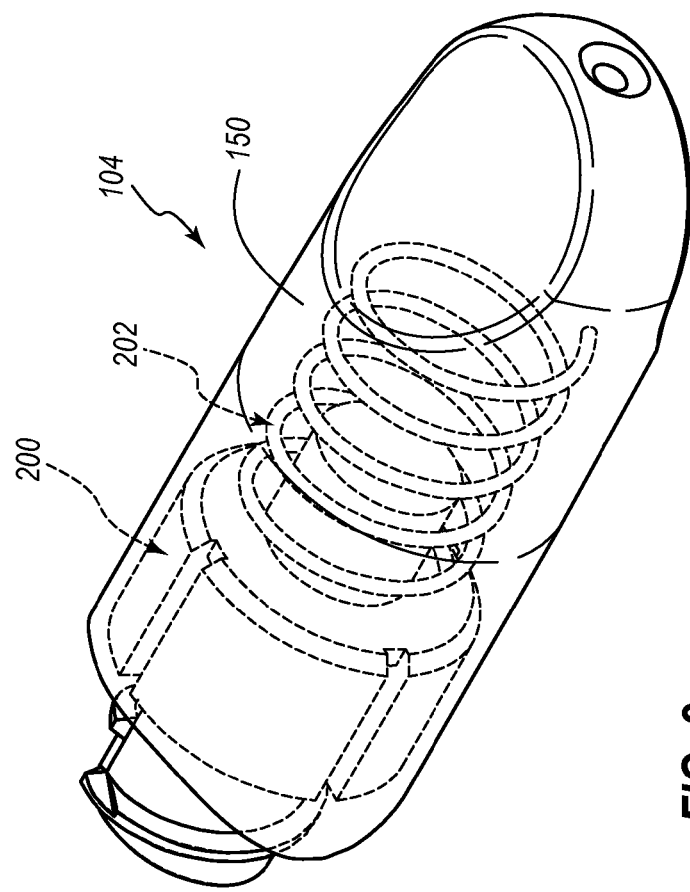
FIG. 2

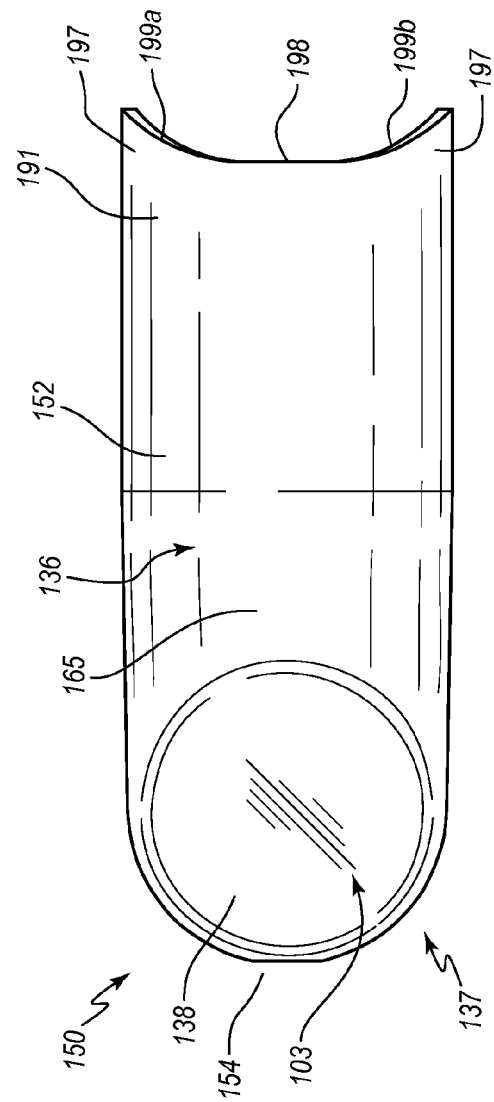
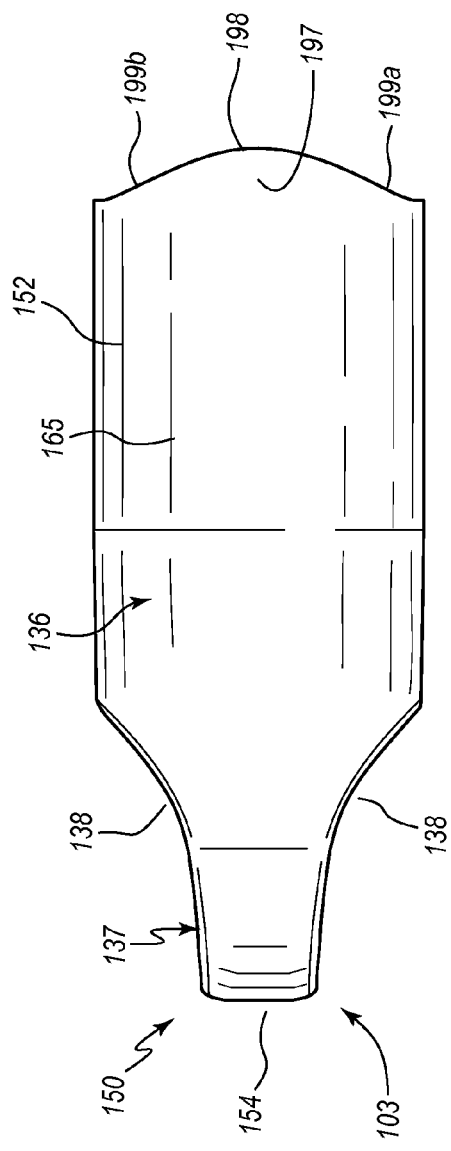
FIG. 5A
FIG. 5B

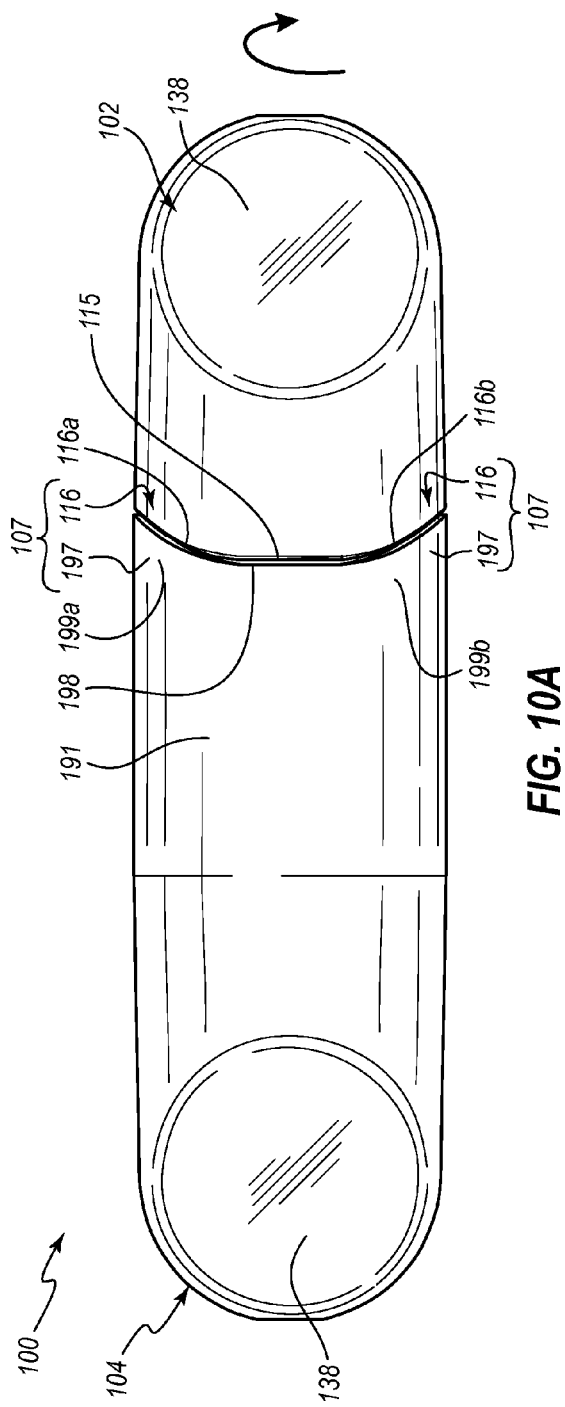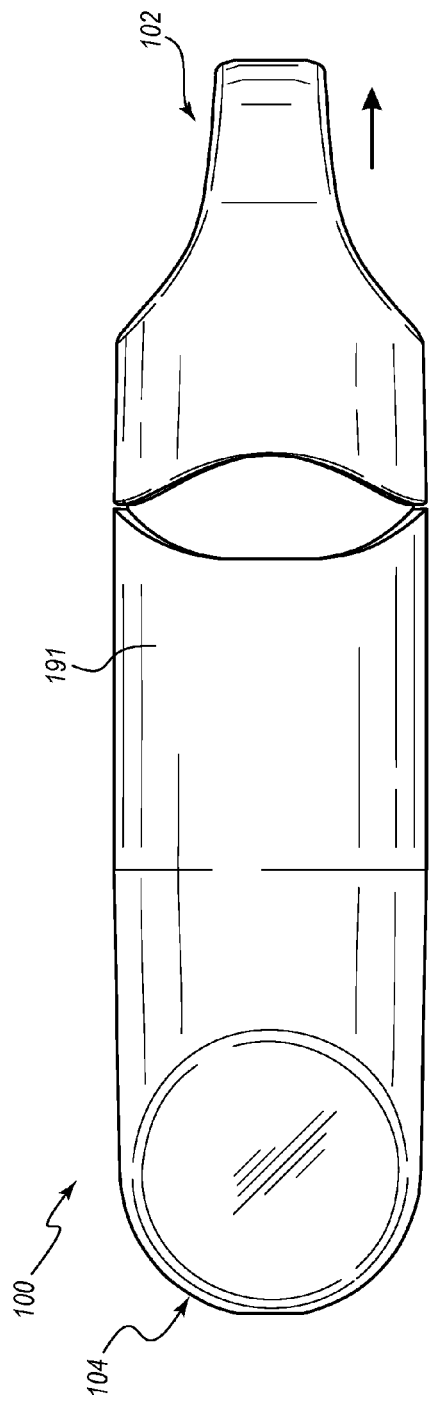

ical Field

The present disclosure generally relates to caps for medical connectors and more specifically relates to caps that can be used to protect the cleanliness of unconnected medical connectors, such as connectors that may be used for fluid flow or for fluid delivery systems. Some embodiments are directed to caps for medical connectors that include elongated male portions.

2. Related Art

Bloodstream infections, such as may be caused by microorganisms that enter patients via intravascular catheters, are a significant cause of illness and excess medical costs. A substantial number of such infections occur in U.S. intensive care units annually. Additionally, a significant fraction of these infections result in death.

Guidelines from the Centers for Disease Control and Prevention describe various ways to limit bloodstream infections in hospital, outpatient, and home care settings. The guidelines address issues such as hand hygiene, catheter site care, and admixture preparation. However, despite these guidelines, such infections continue to plague healthcare systems at relatively unchanged rates.

Impregnating catheters with various antimicrobial agents is one approach for reducing these infections. Impregnated catheters, however, provide less than satisfactory results. Additionally, some microbes have developed resistance to the various antimicrobial agents used in the catheters. Other systems and approaches have also been developed, but these likewise suffer from a variety of limitations and drawbacks.

DISINFECTING CAPS HAVING AN EXTENDABLE FEATURE AND RELATED SYSTEMS AND METHODS

CROSS-REFERENCE TO RELATED APPLICATIONS

This application claims the benefit of U.S. Provisional Patent Application No. 61/265,207, titled DISINFECTANT CAPS AND SYSTEMS AND ASSOCIATED METHODS, filed Nov. 30, 2009; and this application is a continuation-in-part of U.S. patent application Ser. No. 12/917,336, titled DISINFECTING CAPS AND SYSTEMS AND ASSOCIATED METHODS, filed Nov. 1, 2010, which is a continuation-in-part of U.S. patent application Ser. No. 12/610,141, titled STERILIZATION CAPS AND SYSTEMS AND ASSOCIATED METHODS, filed Oct. 30, 2009, the entire contents of each of which are hereby incorporated by reference herein. The earliest date to which this application claims priority is Oct. 30, 2009.

BACKGROUND

1. Technical Field

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2 is a perspective view of the system of FIG. 1 in an open configuration in which the male and female caps are separated from each other;

FIG. 5A is a top plan view of an embodiment of a housing portion of a male cap that is compatible with the assembly of FIG. 1;

FIG. 5B is a side elevation view of the housing portion of the male cap of FIG. 5A;

FIG. 10A is a top plan view of the assembly of FIG. 1 in the pre-use state with an arrow indicating rotation of the female cap relative to the male cap to assist in transitioning the assembly to the open state;

FIG. 10B is another top plan view of the assembly of FIG. 1 showing the female cap having been rotated relative to the male cap so as to assist in translating the female cap away from the male cap;

DETAILED DESCRIPTION

Disclosed herein are caps that can be used to protect and/or disinfect medical connectors. Systems and methods related to such caps are also disclosed. The caps, systems, and methods can reduce the threat of microorganisms entering the bloodstream of a patient via fluid flow or fluid delivery systems, such as, for example, needleless injection sites and/or fluid transfer devices having an elongated male portion or male protrusion, such as, for example, a male luer. In some embodiments, a cap is configured to couple with and disinfect a medical connector having a male protrusion. In further embodiments, the cap can include an antiseptic, and can be configured to create a seal with the male protrusion so as prevent antiseptic from entering a lumen of the male protrusion. In some embodiments, the antiseptic may be contained within a pad prior to the coupling of the cap to the medical connector, and the act of coupling the cap to the medical connector can force at least a portion of the antiseptic from the pad and into contact with the male protrusion. In still further embodiments, the male cap can be coupled with a female cap to form an assembly. The male cap can include a translatable portion that is retained in a retracted position when the assembly is in a pre-use state. Separation of the male and female caps can result in translation of the translatable portion to an extended position that is more readily accessible by a medical connector.

Figure 21:
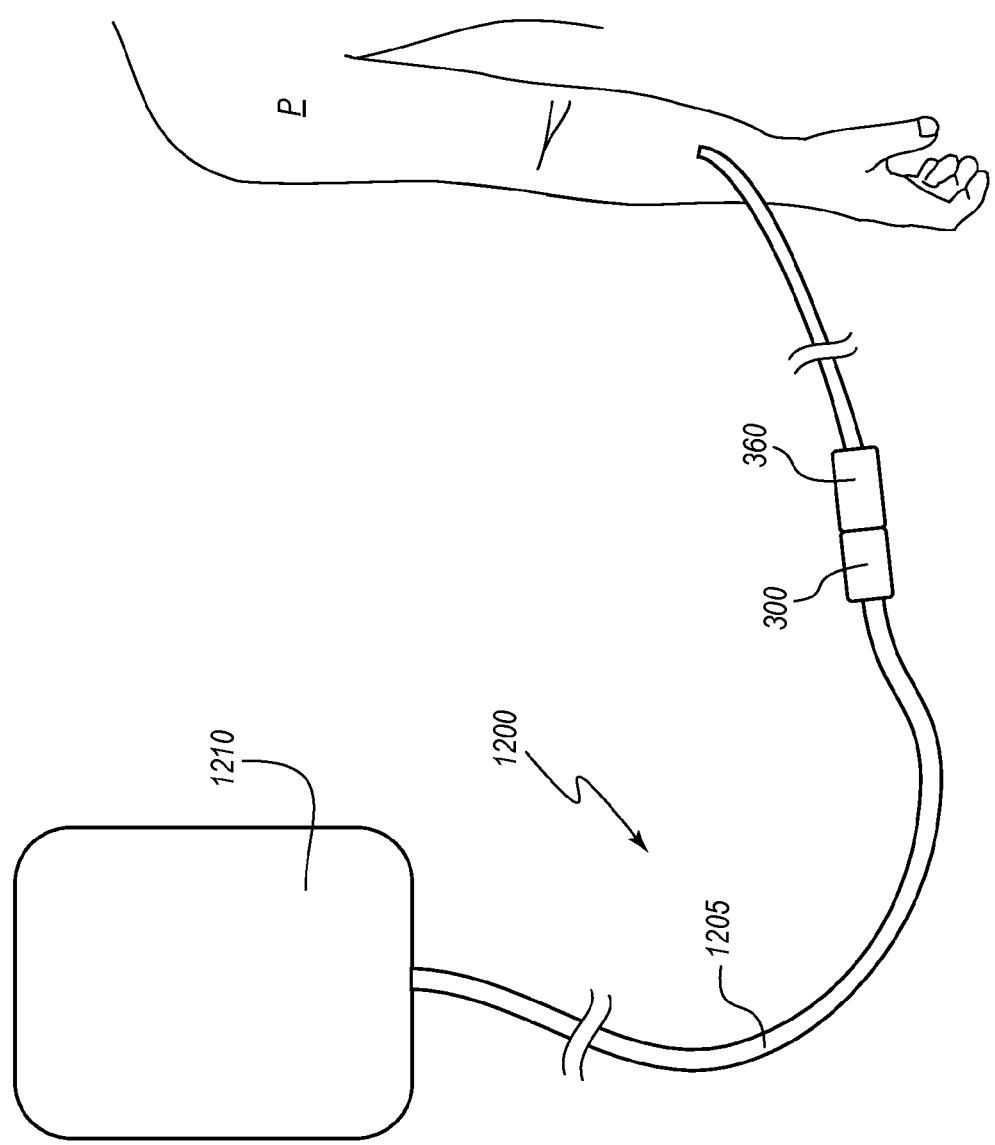
FIG. 21 is a perspective view of a fluid line that includes a coupled set of connectors that are amenable to being coupled with male and female caps, respectively.

By way of background, FIG. 21 illustrates an example of medical connectors 300, 360 for which caps disclosed herein may be used. Any suitable variety of medical connectors 300, 360 is possible, such as, for example, luer lock connectors. The connectors 300, 360 are associated with a fluid pathway 1200, such as a fluid line 1205 of any suitable variety, which may be coupled with an IV bag 1210 or other suitable fluid delivery system. Commonly, the fluid pathway 1200 can be used to intermittently administer medications to a patient P.

In the illustrated embodiment, the connector 360 of the fluid pathway 1200, which communicates fluids with a patient's blood stream, may be selectively disconnected from the connector 300. One or more of the connectors 300, 360 may be connected to other connectors (not shown), such as a connector associated with a central line. The medical connectors 300, 360 may be connected and disconnected at various times, and may remain disconnected for several minutes or hours. Medical connector caps disclosed herein can be used to cover and protect the various medical connectors 300, 360 while the connectors are separated from one another.

Upon separation of the medical connectors 300, 360 from each other, each separated connector can benefit from being covered by a cap. Therefore, in some cases, it can be advantageous to have a single connector set or assembly that includes both a male cap and a female cap that can be used to provide protection for both ends of a separated connection. In other or further embodiments, a cap can include an antiseptic for disinfecting a medical connector. In some cases, it can be advantageous for the cap to form a seal with a portion of the medical connector to thereby prevent the antiseptic from exiting the cap into the fluid pathway. In some embodiments, a male cap includes a translatable portion that is retained in a retracted position when the cap assembly is in a pre-use state. Separation of the male and female caps can result in translation of the translatable portion to an extended position that is more readily accessible by a medical connector.

Figure 1:
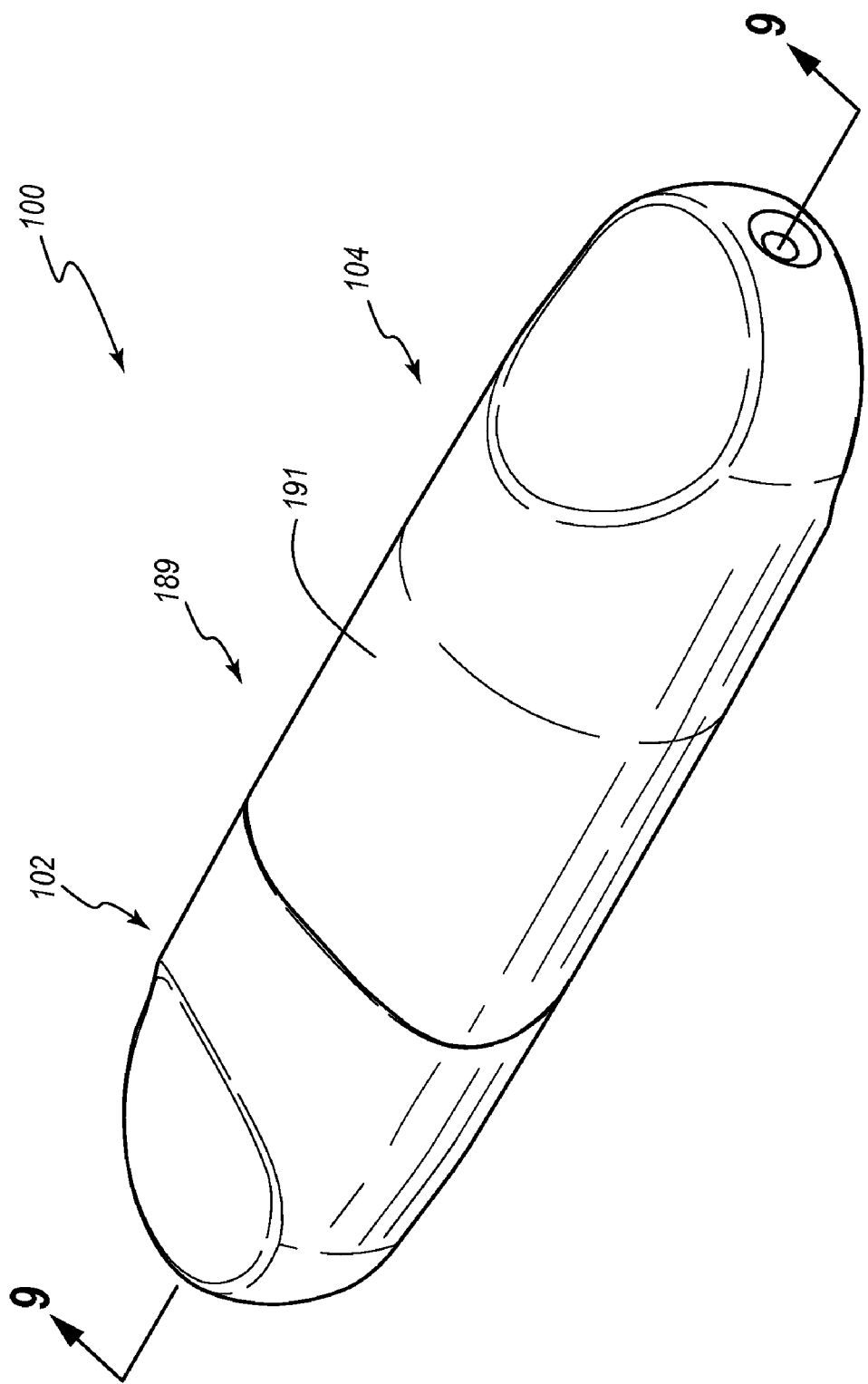
FIG. 1 is a perspective view of an embodiment of an assembly that includes an embodiment of a male cap and an embodiment of a female cap that are coupled with each other in a closed or pre-use configuration.
Figure 3:
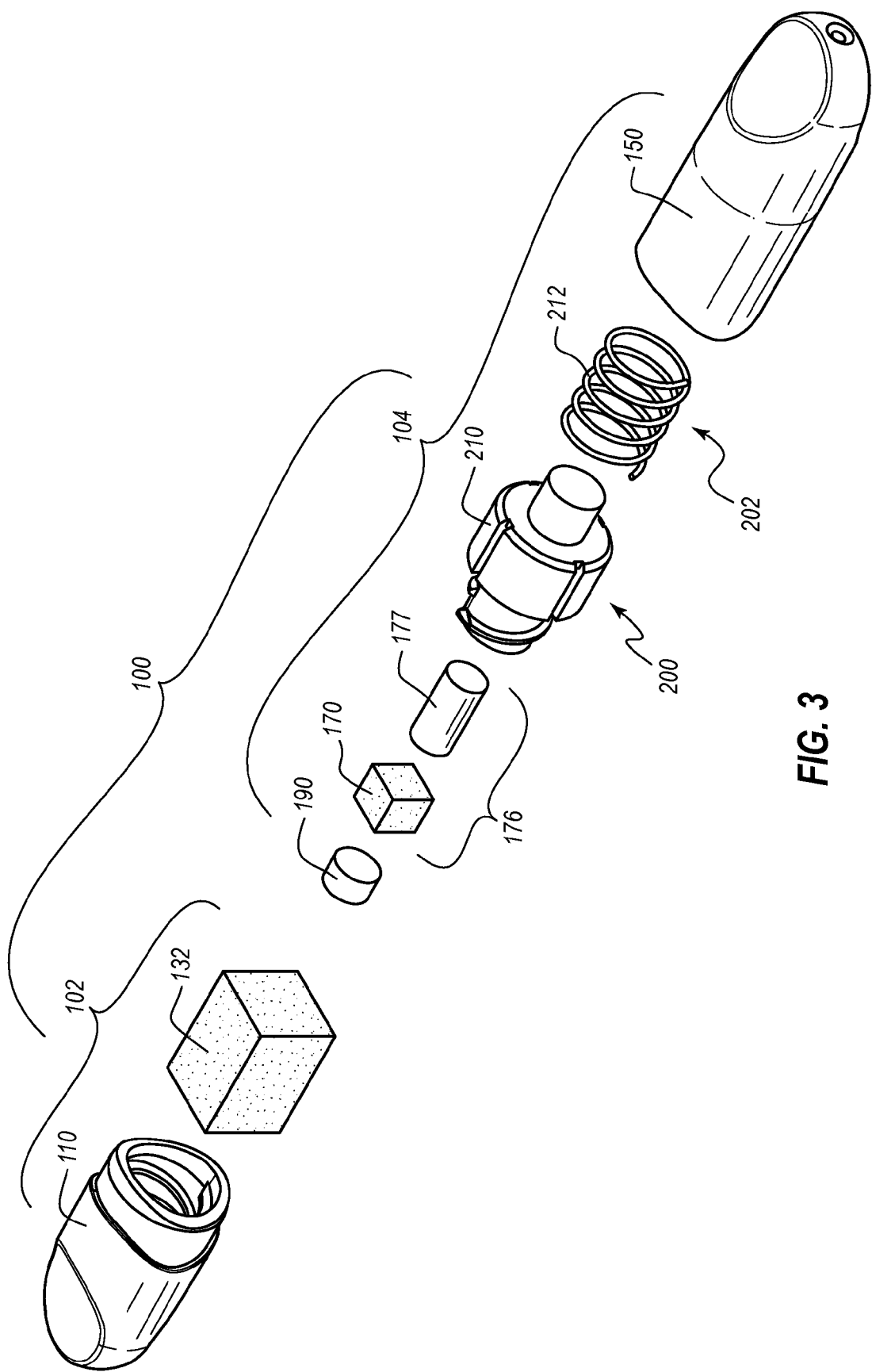
FIG. 3 is an exploded perspective view of the system of FIG. 1.

FIGS. 1-3 illustrate an embodiment of a set or assembly 100 that includes an embodiment of a female cap 102 and an embodiment of a male cap 104, each of which can be used to cover a separated connector 360, 300, respectively. The assembly 100 can be provided in a pre-use, assembled, or closed state in which the female and male caps 102, 104 are coupled with each other, as shown in FIG. 1. As further discussed below, when the caps 102, 104 are coupled with each other, they may form a fluid-tight seal, which can prevent antiseptic from evaporating from an interior of the assembly 100 to an exterior thereof. In particular, the female and male caps 102, 104 can be coupled with each other via a sealing mechanism 189. In the illustrated embodiment, the sealing mechanism 189 comprises a sealing sleeve 191, which is fixedly connected to (e.g., integrally formed with) the male cap 104. The terms "coupled" and variants thereof are used in their ordinary sense and include arrangements such as that illustrated in FIG. 1, in which the caps 102, 104 directly engage one another when the assembly 100 is in the assembled or pre-use state.

As shown in FIG. 2, the female and male caps 102, 104 can be separated from each other. It may be said that the assembly 100 is in an open or operational state when it is in such an arrangement. In the illustrated embodiment, all components of the assembly 100 are contained in or otherwise embodied by one of the female and male caps 102, 104. Accordingly, in some embodiments, the assembly 100 can be devoid of pieces or parts that are readily separable from either of the female and male caps 102, 104 during or after a transition of the assembly 100 from the closed to the open state. Accordingly, the female and male caps 102, 104 each can comprise separate, self-contained, or individual assemblies that may be directly joined to each other, thereby resulting in the composite assembly 100 it its closed state (shown in FIG. 1), and that may be separated from each other, thereby resulting in the disassembled assembly 100 in its open state (shown in FIG. 2). A lack of separate, additional parts when the female and male caps 102, 104 are disconnected from each other can have a variety of advantages. For example, such arrangements can, among other things, provide for a less cluttered work space or environment when one or more of the caps 102, 104 are in use.

As shown in FIG. 2, and as discussed further below, in certain embodiments, the male cap 104 can include an outer housing 150, which can receive a translating or telescoping member, shuttle, or carriage 200. The carriage 200 can be configured to transition between a retracted (e.g., distal) position and an extended (e.g., proximal) position. In FIG. 2, the carriage 200 is in the extended position, whereas it is in the retracted position in FIG. 9, as discussed further below. The male cap 104 can include a biasing member 202, which can be configured to urge or bias the carriage 104 proximally toward the extended position.

The terms "proximal" and "distal," when used herein relative to a cap, or components thereof, are used relative to the coupling of the cap with a medical device, such that the medical device is inserted into a proximal end of the cap, or component thereof and advanced toward a distal end of the cap or component. Accordingly, in the illustrated embodiment, the proximal ends of the caps 102, 104 are directed toward each other and the distal ends of the caps 102, 104 are directed away from each other when the assembly 100 is in the pre-use configuration (see FIG. 1).

FIG. 3 is an exploded view of the assembly 100. The female cap 102 can include a housing 110 into which an antiseptic reservoir or pad 132 is received. As previously mentioned, the male cap 104 can include a carriage 200, which can be configured to receive a resilient support 177, an antiseptic reservoir or pad 170, and a sealing member 190. As further discussed below, the resilient support 177 and the pad 170 may be considered as a multi-part biasing member 176 that is configured to urge the sealing member 190 toward a proximal end of the carriage 200.

As previously mentioned, the housing 150 of the cap 104 can be configured to receive the biasing member 202 and the carriage 200. In the illustrated embodiment, the carriage 200 comprises a movable, translatable, or inner housing 210, and the biasing member 202 comprises a coil spring 212. As further discussed below, the coil spring 212 can be configured to urge the inner housing 210 in the proximal direction, or toward a proximal end of the shell or outer housing 150.

With reference to FIGS. 4A-4C and 9, the housing 110 of the female cap 102 can extend between a closed distal end and an open proximal end. The closed distal end does not permit any fluid flow therethrough and serves as a barrier between an interior of the housing 110 and an exterior environment. The open proximal end of the housing 110 is configured to receive at least a portion of a medical connector therein, as further discussed below with respect to FIGS. 12-14. The housing 110 can include a sidewall 112, which defines the open proximal end, and a base wall 113, which defines at least a portion of the closed distal end.

The housing 110 can include a body region 136 near a proximal end thereof, which is substantially cylindrically shaped in the illustrated embodiment. A handle 137 can extend from the body region 136 so as to be positioned at the distal end of the cap 102. The handle 137 can comprise any suitable gripping features 103, which, in the illustrated embodiment, comprise opposing gripping regions or grasping platforms 138 that are configured to provide a convenient surface against which a user can press so as to hold and/or twist the cap 102.

Figure 4C:
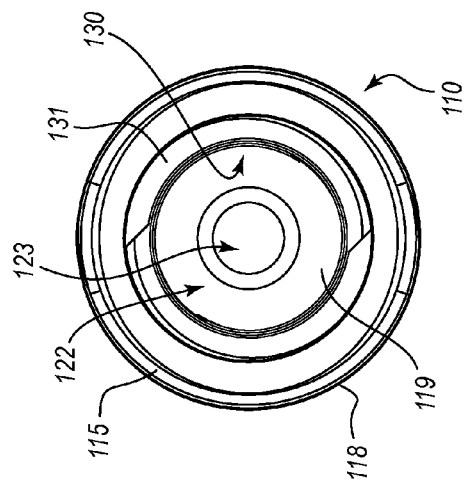
FIG. 4C is a front elevation view of the housing portion of the female cap of FIG. 4A.
Figure 4A:
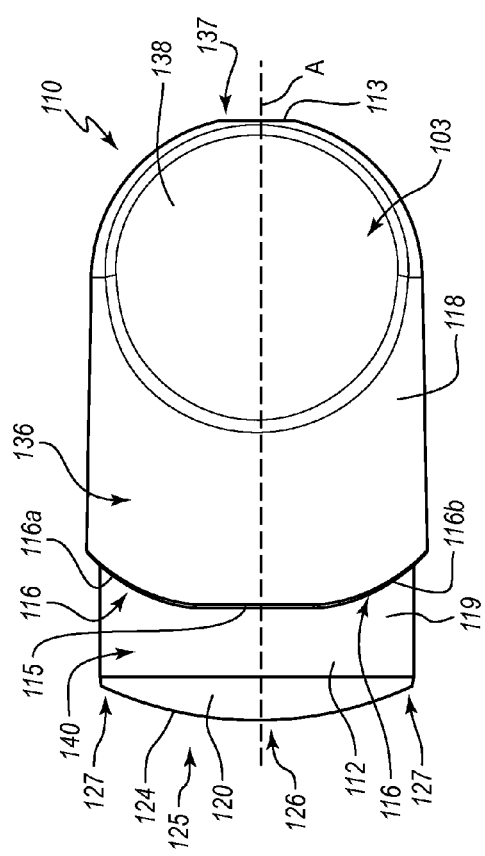
FIG. 4A is a top plan view of an embodiment of a housing portion of a female cap that is compatible with the assembly of FIG. 1.
Figure 4B:
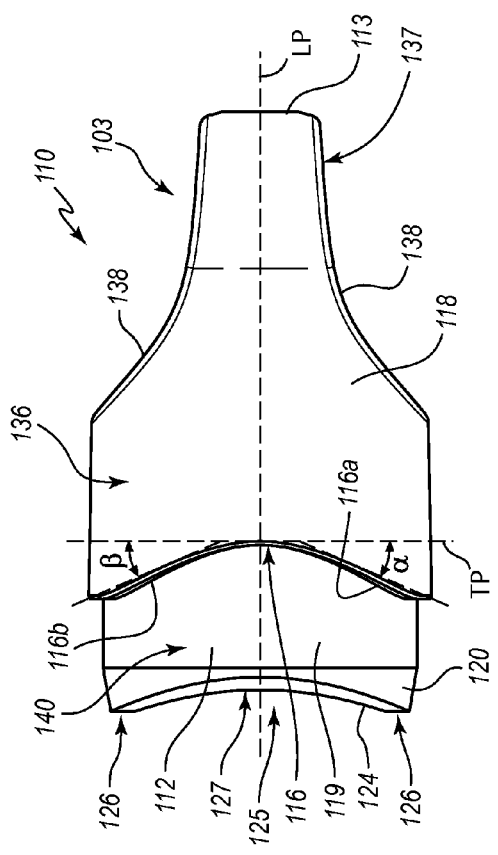
FIG. 4B is a side elevation view of the housing portion of the female cap of FIG. 4A.

As shown in FIG. 4B, the illustrated grasping platforms 138 are mirrored about a longitudinal plane LP that extends along a central longitudinal axis A (shown in FIG. 4A) of the housing 110. Each grasping platform 138 angles radially inwardly from the body region 136 toward the longitudinal plane LP, in a proximal-to-distal direction. The grasping platforms 138 are more steeply angled at their proximal ends than they are at their distal ends. The angled platforms 138, and particularly the steeply angled portions thereof, provide convenient surfaces to which forces may be applied in a distal-to-proximal direction. In the illustrated embodiment, the platforms 138 define two substantially planar regions that are smoothly joined to each other at a rounded transition. The platforms 138 can define a contour that is substantially complementary to fingertips that are pointed in the proximal direction.

As shown in FIG. 4A, the illustrated grasping platforms 138 also taper inwardly toward the central longitudinal axis A of the housing 110 in a proximal-to-distal direction. In the elevation view that is shown, the platforms 138 are substantially ovoid. The platforms 138 are sized and shaped to be held between the fingertips of a thumb and another finger (e.g., the index finger) of a user, although other grasping configurations may also be efficiently employed with the illustrated arrangement. The platforms 138 provide convenient surfaces to which torque may be applied so as to rotate the cap 102 about the longitudinal axis A.

With reference to FIGS. 4A-4C, the cap 102 can include a lip, rim, or flange 115 that extends radially inwardly at a proximal end of the body region 136. The flange 115 can define one or more recesses 116, which can be complementary to features of the male cap 104 so as to define at least a portion of a separation assisting cam, as discussed further below. The flange 115 also can contact an edge of the sleeve 191 portion of the male cap 104 to ensure the desired insertion depth of the cap 102 within the sleeve 191.

With reference again to FIG. 4B, each recess 116 can be at least partially defined by a pair of faces 116a, 116b of the flange 115 that are angled in opposite directions. The angles can be any suitable non-zero, non-180-degree angles relative to a transverse cross-sectional plane TP that passes perpendicularly through the a central axis A of the housing 110. In particular, the faces 116a can define an angle α relative to the transverse plane TP, and the faces 116b can define an angle β relative to the transverse plane TP. In the illustrated embodiment, the angles α, β are the same, although other arrangements are possible (as discussed further below). For a path is traced along the flange 115 in a clockwise direction (when looking toward the flange 115), the path moves proximally along the faces 116a and the path moves distally along the faces 116b. The faces 116a, 116b can be substantially planar over at least a portion thereof, and can be configured to complementarily contact faces of the sleeve 191. Additional discussion of the faces 116a, 116b is provided below with respect to FIGS. 10A-10B.

The housing 110 defines an external surface 118 and an internal surface 119, each of which extends away from the flange 115. The internal surface 119 of the cap 102 can include an outwardly directed surface of the sidewall 112, a proximal end 124 of the sidewall 112, and an inwardly directed surface of the sidewall 112 (see FIGS. 4C and 9). The outwardly directed portion of the internal surface 119 can define a connection interface 140 that is configured to interact with or engage a connection interface 195 of the sleeve 191 (see FIG. 5C) so as to connect the cap 102 to the sleeve 191. In the illustrated embodiment, the connection interfaces 140, 195 couple with each other via a friction-fit engagement. For example, an inner diameter of the connection interface 195 of the sleeve 191 can be slightly smaller than an outer diameter of the connection interface 140 of the cap 102. The friction fit can be sufficiently strong to provide a fluid-tight seal between the cap 102 and the sleeve 191, yet can allow the cap 102 to be removed from the sleeve 191 via manipulation by a user (e.g., without the use of ancillary tools). The fluid-tight seal can prevent evaporative loss of antiseptic from an interior of the assembly 100 when it is in the pre-use configuration and/or can maintain the sterility of the internal portions of the assembly 100. In other or further embodiments, the connection interfaces 140, 195 can include snap-fit devices, threads, and/or any other suitable attachment features. In the illustrated embodiment, a proximal portion of the connection interface 140 includes a chamfer 120, which can assist in centering the cap 102 relative to the sleeve 191 when connecting the cap 102 to the sleeve 191.

The proximal end 124 of the housing 110 (which is also a proximal end of the internal surface 119, or more generally, of the sidewall 112), can define a seal inhibitor 125, which can include one or more contact regions 126 and one or more venting regions 127. In the illustrated embodiment, the seal inhibitor 125 includes two contact regions 126 that are diametrically opposite from each other, and also includes two venting regions 127 that are diametrically opposite from each other and are angularly spaced from the contact regions. Other configurations of the seal inhibitor 125 are also possible, such as, for example, the seal inhibitors discussed in U.S. patent application Ser. No. 12/610,141, titled STERILIZATION CAPS AND SYSTEMS AND ASSOCIATED METHODS, filed Oct. 30, 2009, now published as U.S. Patent Application Publication No. 2010/0049170, which was previously incorporated by reference in this disclosure. Operation of the seal inhibitor 125 is discussed further below with respect to FIG. 13.

Figure 9:
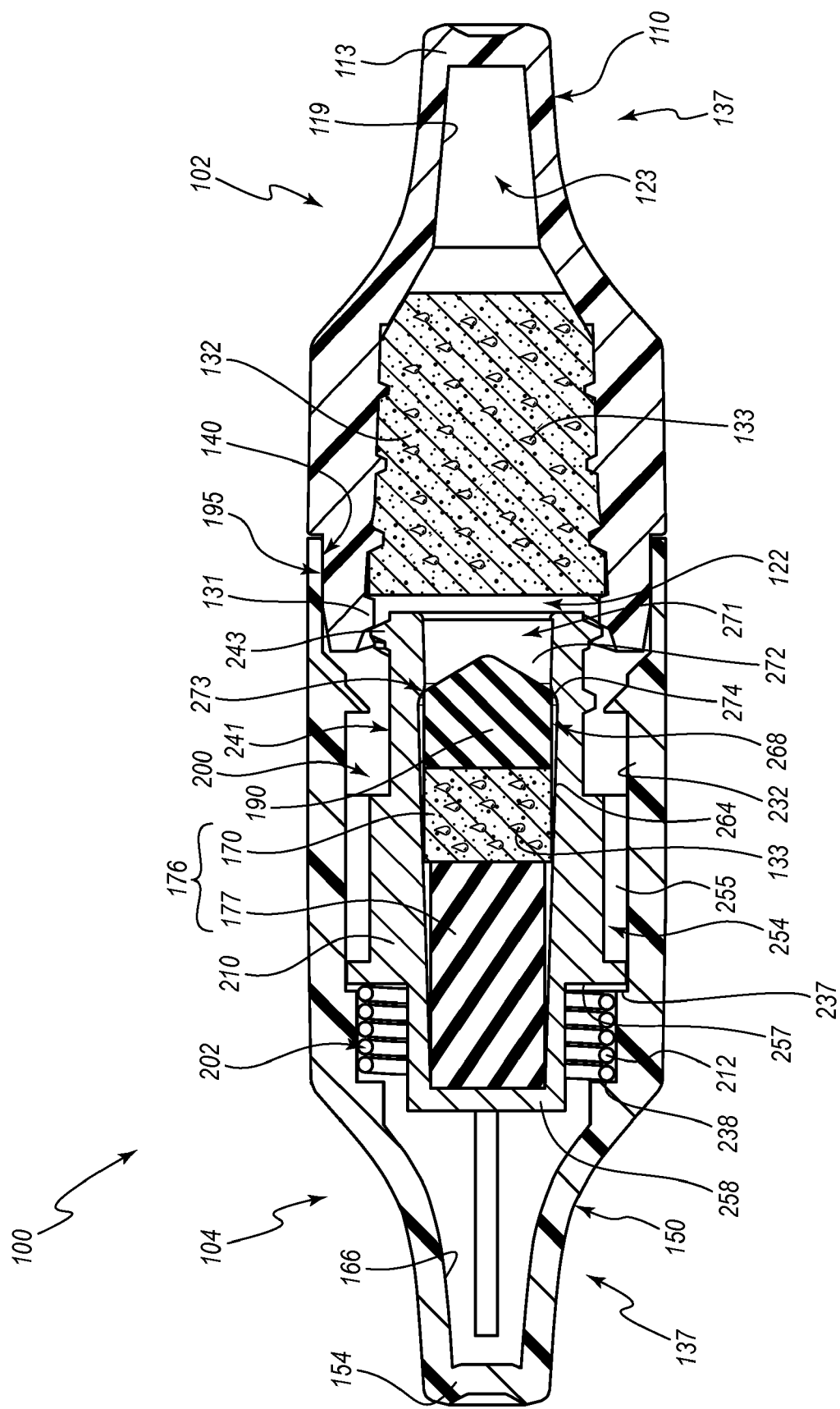
FIG. 9 is a cross-sectional view of the assembly of FIG. 1 in the pre-use state.

With reference to FIGS. 4C and 9, the inwardly directed portion of the internal surface 119 of the sidewall 112 can define a disinfection chamber 122, which can include a connection interface 130. Any suitable connection system may be used for the connection interface 130. In the illustrated embodiment, the connection interface includes threads 131.

The connection interface 130 can be configured to attach the cap 102 to a medical connector in a secure yet selectively removable manner. For example, the cap 102 can be connected in any suitable manner with any suitable medical connector. In other embodiments, the connection interface 130 may include latches or prongs that are configured to snap over an outwardly extending rib of a connector, or may include one or more outwardly extending ribs over which one or more latches or prongs of the medical connector may snap. Other interfacing arrangements are also possible, which may include friction-fit, snap-fit, or other suitable mechanisms.

A proximal portion of the disinfection chamber 122 can be larger than a distal extension 123 of the chamber. In the illustrated embodiment, the disinfection chamber 122 defines three substantially frustoconical regions. The proximal region has a slightly tapered outer boundary that decreases in cross-sectional area in the distal direction; the intermediate region has a more pronounced tapered outer boundary that more rapidly decreases in cross-sectional area in the distal direction; and the distal region or distal extension 123 has a slightly tapered outer boundary that decreases in cross-sectional area in the distal direction at about the same rate as the proximal region. The intermediate and distal regions correspond with the proximal and distal regions, respectively, of the grasping platforms.

As can be appreciated from FIG. 9, the constricted intermediate region of the disinfection chamber 122 can provide a reactive force to a distal end of the pad 132 when the cap 102 is secured to a medical connector. The reactive force can be sufficient to prevent the pad 132 from being forced into the distal extension 123. In the illustrated embodiment, the threads 131 also provide resistive forces. Axial compression of the pad 132 as the cap 102 is coupled to a medical connector can swab the connector and deliver antiseptic 133 from the pad 132 into contact with the medical connector, as further discussed below. In some embodiments, the pad 132 may be resiliently deformable so as to regain a pre-use shape after a medical connector is decoupled from the cap 102. In other embodiments, the pad 132 may instead be plastically deformable.

In various embodiments, the pad 132 can be configured to retain an antiseptic 133. For example, the pad 132 can comprise any suitable sponge-like material, such as an elastomeric foam, any open-cell foam, felt, or non-woven fiber matrix, and can be configured to conform to the contours of a portion of a medical connector that is introduced into the disinfection chamber 122 (e.g., uneven surfaces of an end of a needleless injection site; see also FIGS. 12-14 and the associated written description). The pad 132 can also comprise any closed-cell foam, as well as a solid elastomeric material, such as silicone or the like.

The pad 132 can have a series or network of openings or spaces therein that can retain the antiseptic 133 when the pad 132 is in an expanded state. For example, the antiseptic 133 can be received within, occupy, fill (or partially fill), wet, soak, or saturate at least a fraction of the pad 132, or stated otherwise, can fill the pad 132 to a given concentration level. Compression of the pad 132 can cause antiseptic 133 to egress from the pad 132 so as to contact the medical connector. Resilient expansion of the foam upon removal of a compressive force can allow the pad 132 to soak up or absorb at least some of the antiseptic 133 that had previously been forced from the pad 132. In some embodiments, the antiseptic 133 can comprise any liquid antiseptic, such as, for example, alcohol (e.g., isopropyl alcohol) at various concentrations (e.g., ranging from 50-90%), ethanol at various concentrations (e.g., ranging from 50-95%), and combinations of any alcohols with any antiseptics, or a dry material, such as chlorhexidine, ethylenediaminetetraacetic acid (EDTA), lodaphors, or any suitable combination thereof. Accordingly, although the antiseptic 133 is schematically depicted in FIG. 1 as a series of droplets, the antiseptic 133 is not necessarily liquid and may fill the pad 132 to a greater or lesser extent than what is shown. In the illustrated embodiment, when the assembly 100 is in the pre-use condition, the pad 132 is in a relaxed, expanded, or uncompressed state in a longitudinal direction. It is noted that the pad 132 may be uncompressed in one or more dimensions, yet compressed in one or more other dimensions, when the assembly 100 is in the pre-use state. For example, the pad 132 can be expanded or in a relaxed state in a longitudinal direction, yet compressed radially inwardly via the sidewall 112, when the assembly 100 is in the pre-use state.

In the illustrated embodiment, the pad 132 is substantially square in cross-section along its full longitudinal length when the pad 132 is in a relaxed orientation (see FIG. 3). Such an arrangement can facilitate and/or reduce material costs associated with the manufacture of the pad 132. At least a portion of the pad 132 (e.g., the corners thereof) may be compressed radially when the pad 132 is positioned within the housing 112. Other rectangular cross-sections are also possible for the pad 132, and in other or further embodiments, the pad 132 may define a rectangular cross-section along only a portion of the longitudinal length thereof. In other embodiments, at least a portion of the pad 132 may define a round cross-section, such as a circular, elliptical, or other ovoid shape. For example, the pad 132 can be cylindrical so as to have a circular cross-section. The pad 132 may define any other suitable shape, and may or may not be radially compressed when the assembly 100 is in the pre-use state.

Figure 5C:
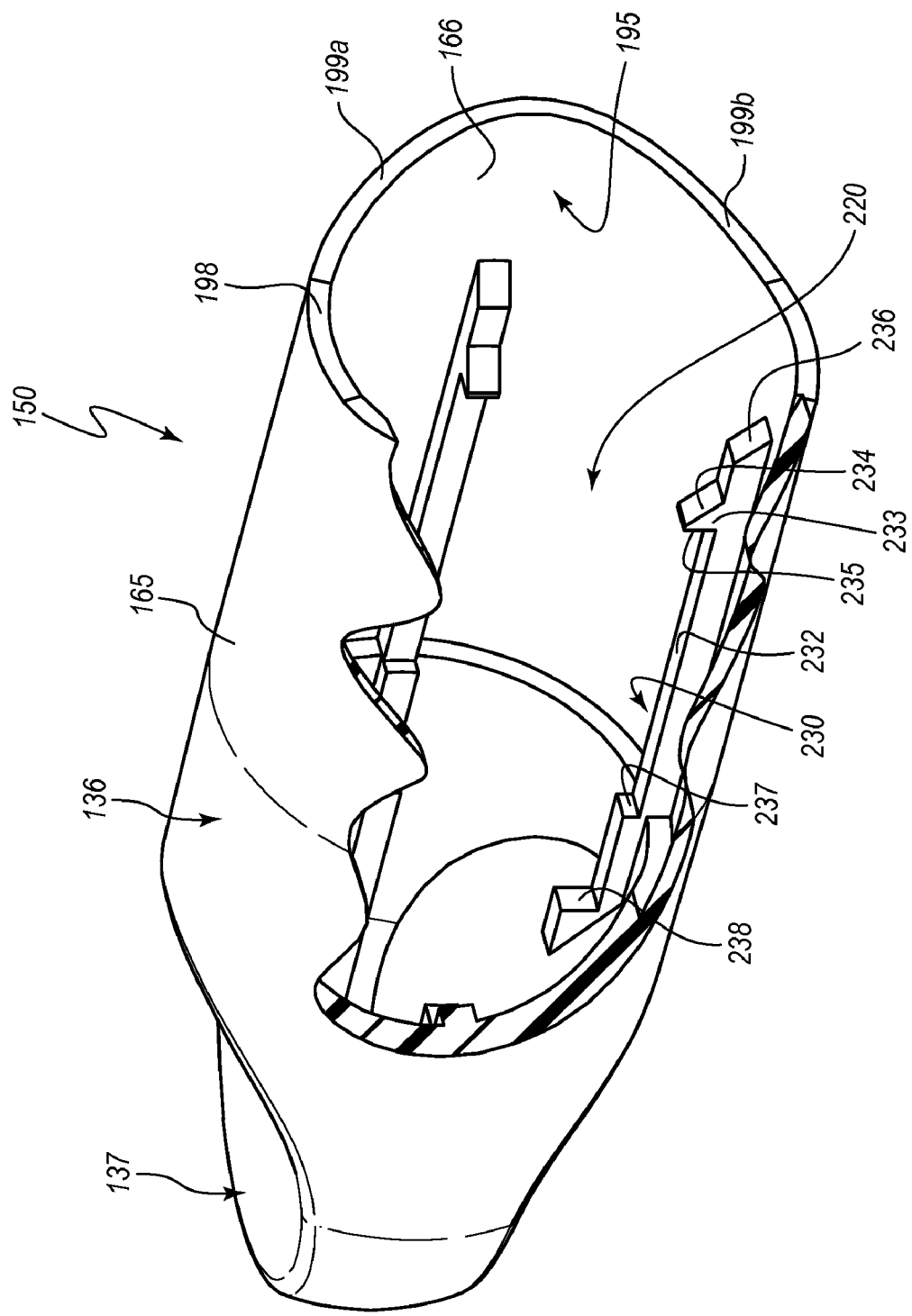
FIG. 5C is a cutaway perspective view of the housing portion of the male cap of FIG. 5A.

With reference to FIGS. 5A-5C, the housing 150 of the male cap 104 can extend between a closed distal end and an open proximal end. The closed distal end does not permit any fluid flow therethrough and serves as a barrier between an interior of the housing 150 and an exterior environment. The open proximal end of the housing 150 is configured to receive at least a portion of a medical connector therein and/or to permit passage of at least a portion of the carriage 200 therethrough.

As viewed from the exterior (e.g., in FIGS. 5A and 5B), a shape and/or configuration of the distal end of the housing 150 can be similar or identical to the distal end of the housing 110 of the female cap 102, which is discussed above. For example, in the illustrated embodiment, the housing 150 includes a body region 136 and a handle 137 with grasping platforms 138, which when viewed exteriorly, are identical to the identically numbered features of the cap 102. Accordingly, as can be seen in FIGS. 1 and 10A, when the assembly 100 is in the pre-use state, distal ends of an exterior thereof can be symmetrical about three mutually perpendicular planes. Other arrangements are also possible.

With continued reference to FIGS. 5A-5C, the housing 150 can include one or more protrusions 197 that are configured to mate or cooperate with the recesses 116 of the female cap 102. In particular, each pair of coupled protrusions 197 and recesses 116, or portions thereof, can operate as a separation assist 107, as further discussed below with respect to FIGS. 10A and 10B. The housing 150 can include a lip, rim, or flange 198 that extends radially inwardly at a proximal end of the sleeve 191. The housing 150 can define an external surface 165 and an internal surface 166, each of which extends away from the flange 198. The internal surface 166 of the cap 104 can define the connection interface 195 discussed above.

The flange 198 can contact the flange 115 of the female cap 102, which can ensure the desired insertion depth of the cap 102 within the sleeve 191. At least a portion of the flange 198 can be shaped complementarily to the flange 115 of the cap 102. With reference to FIGS. 5A and 5B, the flange 198 can define a pair of faces 199a, 199b that are angled in opposite directions.

With reference to FIG. 5C, the housing 150 can define a receptacle or cavity 220 within which the carriage 200 may move between the retracted and extended positions. The housing 150 can further define one or more movement constraining members 230, which may extend inwardly from (e.g., project inwardly) or extend outwardly from (e.g., be recessed relative to) the interior surface 166 of the housing 150. For example, the housing 150 can include one or more, two or more, three or more, or four or more movement constraining members 230. The illustrated embodiment includes four movement constraining members 230 (only two of which are shown in FIG. 5C) that are angularly spaced from each other at approximately 90 degree intervals. Other suitable arrangements are also possible.

In the illustrated embodiment, each constraining member 230 comprises an inwardly projecting track, protrusion, or spline 232. Each illustrated spline 232 includes a proximal stopping member or stop 233, which can comprise a lock, latch, detent, or any other suitable stopping mechanism. In the illustrated embodiment, each proximal stop 233 is substantially wedge shaped and includes a distally angled entry face 234, which can facilitate an overriding force or snap fit during manufacturing, and a transversely extending locking face 235. The splines 232 also can include transversely extending distal stopping faces 237, 238. In the illustrated embodiment, the splines 232 are elongated structures (e.g., ribs) that extend substantially parallel to each other. In particular, the splines 232 are elongated in the longitudinal direction, and each may be substantially parallel to a longitudinal axis defined by the housing 150. In some embodiments, the splines 232 can have a helical configuration, which can resist distal movement of the carriage 200 when the male cap 104 is coupled with a medical connector. Other suitable arrangements of the splines 232 are also contemplated.

Figure 6:
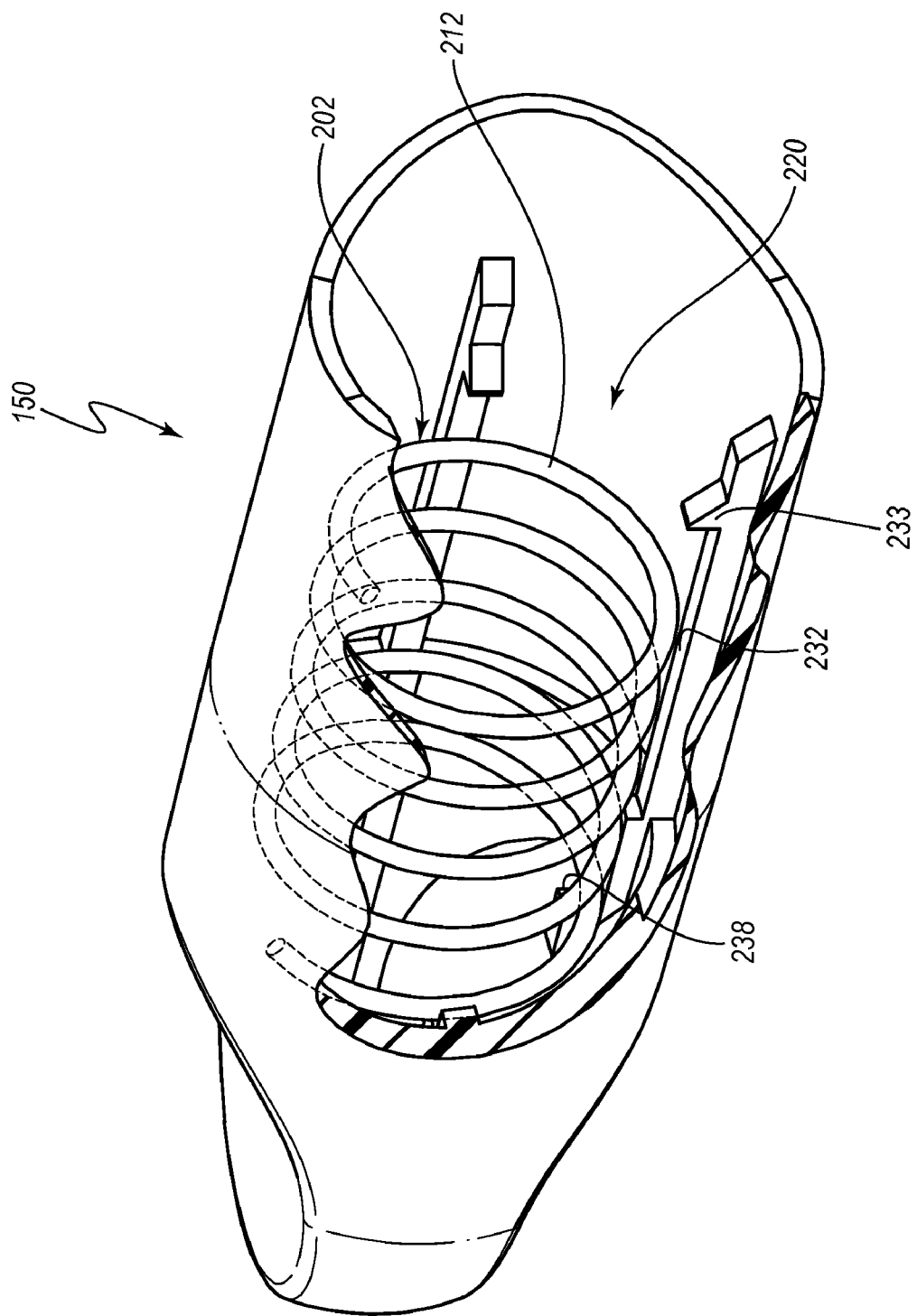
FIG. 6 is a cutaway perspective view of the housing portion of the male cap, as shown in FIG. 5C, with an embodiment of a biasing element disposed therein.

With reference to FIG. 6, the biasing member 202, which is a coil spring 212 in the illustrated embodiment, can be received within the cavity 220. A distal end of the coil spring 212 can contact the distal stopping surface 238, such that the distal stopping surface 238 can act as a resistive surface against which, or toward which, the coil spring 212 can be compressed. In other embodiments, the biasing member 202 can comprise any other suitable device that is configured to urge the carriage 200 in the proximal direction. For example, the biasing member 202 can comprise a resiliently deformable pad or support post of any suitable material, such as those described elsewhere herein. In other or further embodiments, the biasing member 202 can comprise one or more springs that are in forms other than helical, such as, for example, beam, leaf, conical, torsion, etc. Such springs may comprise any suitable material, such as, for example, metals and/or polymers. In some embodiments, the biasing member 202 may be formed integrally with the outer housing 150 and/or the inner housing 210.

Figure 7:
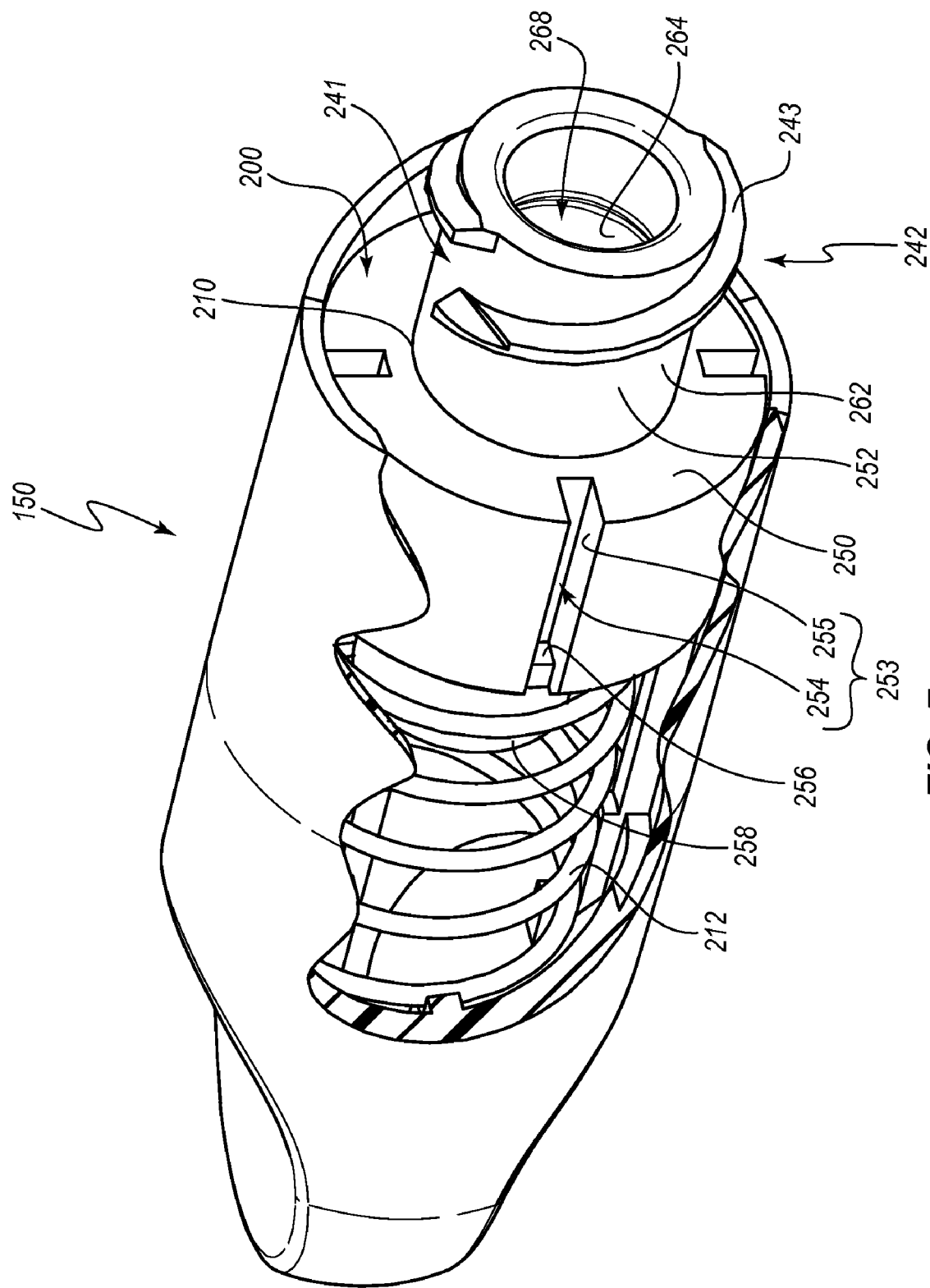
FIG. 7 is a cutaway perspective view of the housing portion of the male cap, as shown in FIG. 5C, with both an embodiment of a biasing element and an embodiment of a carriage disposed therein.
Figure 8:
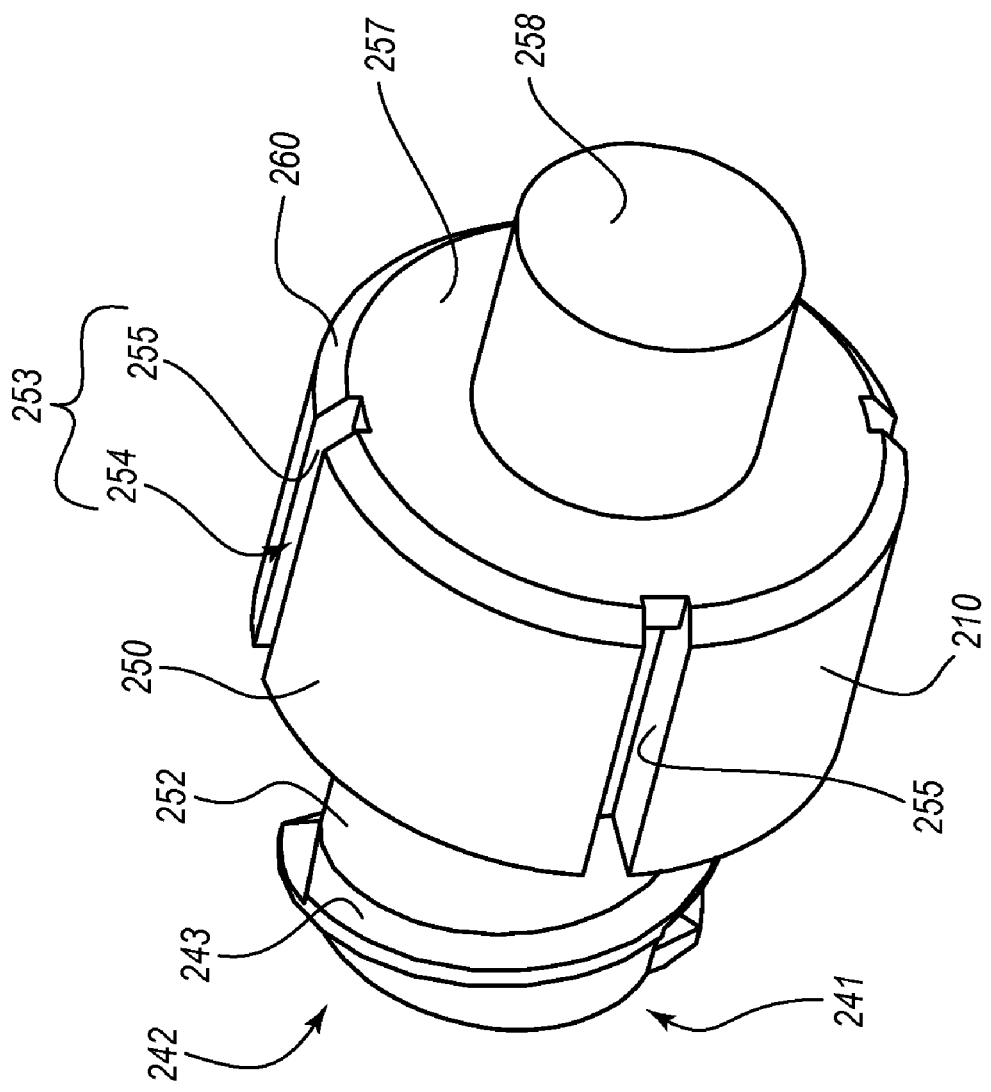
FIG. 8 is a rear perspective view of the carriage that is also shown in FIG. 7.

With reference to FIG. 7, the carriage 200 can be received within the cavity 220 and positioned at a proximal end of the spring 212. As shown in FIGS. 7 and 8, the inner housing 210 of the carriage 200 can comprise a body or base 250 that is sized and shaped to translate along a longitudinal path through the cavity 220. In the illustrated embodiment, the base 250 is substantially cylindrical. The base 250 can include a proximal extension 252, which may define a smaller outer diameter than the base 250. The illustrated proximal extension 252 is also substantially cylindrical, and is coaxial with the base 250.

The inner housing 210 can include one or more movement constraining members 253, which can be configured to cooperate with the movement constraining members 230 of the outer housing 150 in order to constrain, guide, or otherwise control movement of the inner housing 210 within the outer housing 150. For example, the constraining members 253 of the inner housing 210 can be complementarily shaped relative to the constraining member 230 of the outer housing 150. In the illustrated embodiment, each constraining member 253 of the inner housing 210 comprises a groove or channel 254 that is sized to receive at least a portion of a spline 232. Accordingly, in the illustrated embodiment, the inner housing 210 comprises four channels 254 that are angularly spaced from each other by about 90 degrees.

The channels 254 can be configured to readily slide, glide, or otherwise translate over the splines 232. Each channel 254 can be defined by sidewalls 255, which may be substantially planar so as to smoothly pass over substantially planar walls of the splines 232. Moreover, the sidewalls 255 may cooperate with the walls of the splines 232 to limit, inhibit, or prevent rotation of the inner housing 210 relative to the outer housing 150. Other suitable arrangements for the constraining members 230, 253 are also possible. For example, in other embodiments, the constraining members 230 of the outer housing 150 may comprise channels, whereas the constraining members 253 of the inner housing 210 can comprise outwardly projecting splines that can translate within the channels. In arrangements where the movement constraining members 230, 253 are configured to prevent or inhibit rotation of the inner housing 210 relative to the outer housing 150, the movement constraining members 230, 253 may also be referred to as anti-rotation members.

As previously mentioned, in other embodiments, the splines 232 may be substantially helical. The channels 254 and sidewalls 255 thus may likewise define a substantially helical shape so as to appropriately interface with the helical splines 232. In such an embodiment, the movement constraining members 230, 253 thus may permit rotational movement between the inner housing 210 and the outer housing 150, although the path of this rotational movement can be controlled by the movement constraining members 230, 253. Stated otherwise, the movement constraining members 230, 253 can be configured to permit controlled, constrained, or limited rotational movement of the inner housing 210 relative to the outer housing 150. A pitch of the helical constraining members 230, 253 can be selected to achieve a desired operation of the male cap 104. For example, the pitch may be selected so as to allow the biasing member 202 to move the carriage 200 proximally.

In the illustrated embodiment, each channel 254 includes a distal stopping member or stop 256, which can comprise a lock, latch, or any other suitable stopping mechanism. In the illustrated embodiment, each distal stop 256 includes a substantially transversely extending face that is configured to contact the transversely extending locking faces 235 of the proximal stops 233. The distal stops 256 of the inner housing 210 thus can cooperate with the proximal stops 233 of the outer housing 150 to limit the translational movement of the inner housing 210. In particular, the stops 233, 256 can cooperate to prevent the inner housing 150 from being pushed proximally out of the housing 150 by the coil spring 212.

The base 250 of the inner housing 210 can include a distal surface 257. A distal projection 258 can extend distally from the surface 257. In the illustrated embodiment, the distal projection 258 is substantially cylindrical and is sized to be received within the coil spring 212. The distal projection 258 can maintain the inner housing 210 in a centered orientation relative to the spring 212.

In the illustrated embodiment, the base 250 of the inner housing 210 includes a chamfer 260, which can assist in assembly of the male cap 104. In particular, the chamfer 260 can aid in centering the inner housing 210 relative to the outer housing 150 when the inner housing 210 is inserted into the outer housing 150.

An open proximal end of the inner housing 210 can be sized and shaped to receive at least a portion of a male protrusion of a medical connector. For example, the open proximal end of the housing 210 can be configured to receive at least a portion of a male luer. The open end of the housing 210 and the male luer can comply with ISO standards (e.g., ISO 594-1:1986 and ISO 594-2:1998). Other arrangements are also possible.

Figure 11A:
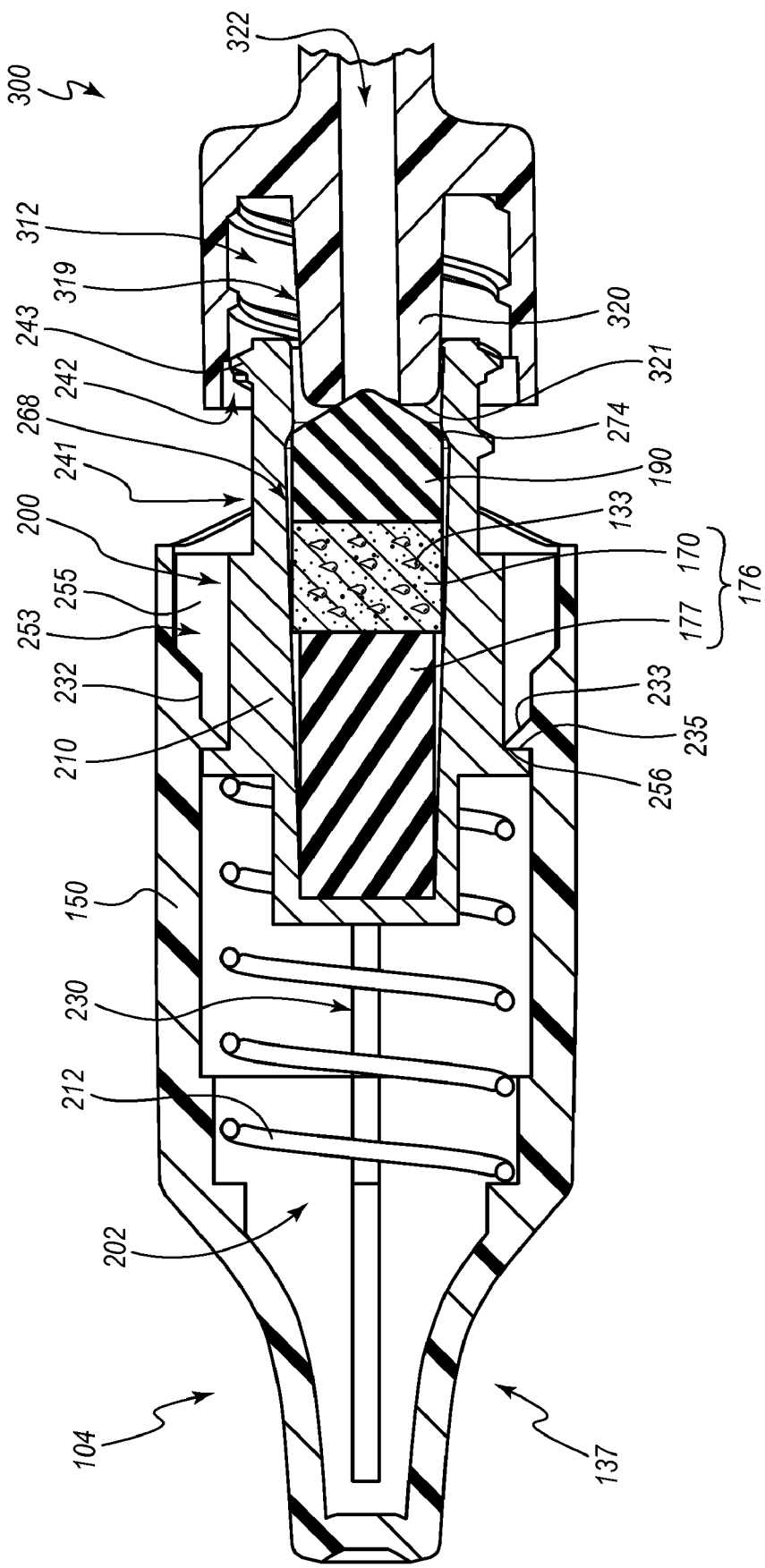
FIGS. 11A-11D are cross-sectional views that depict various stages of an illustrative method for coupling a medical connector with the male cap of FIG. 1.

The proximal extension 252 described above may also be referred to more generally as a male projection 241 portion of the inner housing 210. The projection 241 can be configured to couple with a medical connector that includes a male protrusion. The projection 241 includes a connection interface 242 that is configured to effect the coupling. In the illustrated embodiment, the projection 241 is substantially cylindrical, and the connection interface 242 comprises one or more threads 243 that are positioned at an outwardly facing surface of the cylinder. Any other suitable connection interface 242, such as any of those described above, is possible. As can be seen in FIGS. 7, 9, and 11A, the connection interface 242 can be at an interior of the outer housing 150 when the inner housing 210 is in the retracted position, and at least a portion of the connection interface 242 can be at an exterior of the outer housing 150 when the inner housing 210 is in the extended position.

With reference to FIGS. 7 and 9, an inner surface 264 of the inner housing 210 can define a disinfection chamber 268. As shown in FIG. 9, a proximal portion of the disinfection chamber 268 can include a proximal seal region 271, which can be configured to form a fluid-tight seal with the male protrusion portion of a medical connector. For example, the seal region 271 may be shaped complementarily to an outer surface of a male protrusion of a medical connector with which the male cap 104 is configured to be used. In the illustrated embodiment, the proximal seal region 271 comprises a substantially frustoconical surface 272 that complies with ISO luer standards, as discussed above, such that a portion of a male luer can form a seal with the seal region 271. The frustoconical surface 272 can be tapered so as to decrease in diameter in a distal direction. In other embodiments, the proximal portion of the disinfection chamber 268 may not be configured to form a fluid-tight seal with a male protrusion of a medical connector.

With continued reference to FIG. 9, the disinfection chamber 268 can further include an intermediate seal region 273. In the illustrated embodiment, the intermediate seal region is formed by a rim, ridge, lip, or shelf 274, which is defined by a short, substantially frustoconical portion of the inner housing 210 that increases in diameter in the distal direction. An outer edge of a proximal surface of the sealing member 190 can define a greater outer diameter than a minimum inner diameter of the shelf 274 such that the shelf 274 can maintain the sealing member 190 within the chamber 268. The shelf 274 also can cooperate with the sealing member 190 to seal the chamber 268 when the assembly 100 is in the pre-use state, as further discussed below.

A distal end of the resilient support 177, which may also be referred to as a post or a base element, can abut an inner surface of the distal projection 258 of the inner housing 210. The resilient support 177 can be configured to provide a base against which the antiseptic reservoir or pad 170 can be compressed so as to force antiseptic 133 therefrom. Accordingly, the resilient support 177 can be harder, stiffer, or less compliant than the pad 170, and can be configured to compress, under a given force, to a smaller extent than the pad 170 does under the same force. For example, in various embodiments, the resilient support 177 can be no less than about 2, 3, or 4 times harder than the pad 170.

The resilient support 177 can be elastically deformable such that compression of the support 177 from a relaxed orientation gives rise to a restorative force. The resilient support 177 can naturally return to the relaxed orientation upon removal of the compressive force. The resilient support 177 can comprise any suitable elastically deformable material. In some embodiments, the resilient support 177 comprises an elastomeric material, such as silicone. In certain embodiments, the resilient support 177 comprises a closed configuration (e.g., closed cell foam) or is otherwise nonabsorbent such that little or no antiseptic 133 that is expelled from the pad 170 is received into the resilient support 177. In other or further embodiments, the resilient support 177 may comprise a spring (e.g., a compression coil spring). In other embodiments, such as mentioned elsewhere herein, a resilient support 177 is not used.

The pad 170 can comprise any suitable material, such as those described above with respect to other pads (including plastically deformable materials, in some instances), and may be elastically or resiliently deformable. In some embodiments, the pad 170 is attached to the resilient support 177 via any suitable adhesive or other attachment mechanism, although in other embodiments, no such attachment mechanisms are used. For example, the pad 170 and the resilient support 177 may be maintained in contact with each other due to a slight longitudinal compression of one or more of these components once the cap 104 is assembled (e.g., once the support 177, the pad 170, and the sealing member 190 are positioned between the support post 168 and the shelf 174). Similarly, the pad 170 may be attached to the sealing member 190, or it may maintain a substantially fixed orientation relative to the sealing member 190 without such attachment due to the resilience of the pad 170 and/or the support 177, which are in a slightly compressed state.

In the illustrated embodiment, the pad 170 is substantially square in cross-section along its full longitudinal length when the pad 170 is in a relaxed orientation (see FIG. 3). Such an arrangement can facilitate and/or reduce material costs associated with the manufacture of the pad 170. At least a portion of the pad 170 (e.g., the corners thereof) may be compressed radially when the pad 170 is positioned within the inner housing 210. Other rectangular cross-sections are also possible for the pad 170, and in other or further embodiments, the pad 170 may define a rectangular cross-section along only a portion of the longitudinal length thereof. In other embodiments, at least a portion of the pad 170 may define a round cross-section, such as a circular, elliptical, or other ovoid shape. For example, the pad 170 can be cylindrical so as to have a circular cross-section. The pad 170 may define any other suitable shape, and may or may not be radially compressed when the assembly 100 is in the pre-use state.

As previously mentioned, the pad 170 and the support 177 can, in some embodiments, cooperate as a two-part biasing member 176. It is to be understood that any other suitable biasing member 176 may be used, such as those described above. The biasing member 176 can urge the sealing member 190 in the proximal direction into sealing contact with the shelf 274. The seal thus formed may be fluid-tight, and may prevent antiseptic 133, whether in liquid or vapor form, from exiting the disinfecting chamber 268 prior to coupling of the male cap 104 to a medical connector. This proximal seal may be in place when the assembly 100 is in the pre-use configuration, as well as after the separation of the male and female caps 104, 102 when the assembly 100 is opened.

The illustrated sealing member 190 comprises unitary piece of material that includes a cylindrical region and a conical region. The conical region can be well-suited to form a seal with a tip of the projection of a male medical connector. In some instances, an apex of the conical region can be received within a lumen 322 of a luer 320 when a medical connector is coupled with the cap 104 (see, e.g., FIG. 11A). The sealing member 190 can be formed of any suitable material, such as, for example, an elastomer (e.g., silicone) or a thermoplastic, such as polypropylene, polycarbinate, acrylonitrile butadiene styrene (ABS), polyvinyl chloride (PVC), or rigid or semi-rigid thermoset plastic. The sealing member 190 can be formed in any suitable fashion, such as via molding or die cutting. In some embodiments, the sealing member 190 can be harder, more rigid, and/or less compliant than the pad 170. The sealing member 190 may be integral to the pad 170. For example, in some embodiments, the sealing member 190 may comprise a skin that is applied to the pad 170, or may comprise a modification of a surface of the pad 170 (e.g., melting, heat forming, or the like). Other shapes of the sealing member 190 are possible, including, for example, flat or planar, disk-shaped, spherical, etc.

When the assembly 100 is in the pre-use state shown in FIG. 9, the coil spring 212 can be in a compressed state such that a biasing force tends to urge the carriage 200 in the proximal direction. This biasing force can be countered by interacting or cooperating surfaces of the inner male housing 210 and the female housing 110. In the illustrated embodiment, a proximal end or portion of the threads 243 of the inner male housing 210 and a proximal end or portion of the threads 131 of the female housing 110 contact each other and thereby cooperate to prevent proximal movement of the carriage 200. In further embodiments, the proximal portions of the threads 131, 243 may engage one another. For example, the caps 102, 104 may be rotated relative to each other during the manufacture of the assembly 100 so as to cause the threads 131, 243 to engage each other.

Other suitable arrangements or cooperating features may be used to urge the carriage 200 into the retracted position and/or to retain the carriage 200 in the retracted position. For example, in some embodiments, cooperating tabs or flanges that are separate from the threads 131, 243 may be used.

The connection interface 195 of the male cap 104 and the connection interface 140 of the female cap 102 can cooperate with each other to maintain the assembly 100 in the pre-use configuration. Any suitable connection interfaces may be used for this purpose. In the illustrated embodiment, the connection interface 195 of the male cap 104 comprises a region of the proximal end of the outer housing 150, and the connection interface 140 of the female cap 102 comprises a region of the proximal end of the housing 110. An inner surface of the proximal region of the outer housing 150 defines a similarly sized or smaller inner diameter than does an outer surface of the proximal end of the housing 110 of the female cap 102, such that the proximal regions of the housings 150, 110 can be tightly or securely fastened to each other in a friction fit. The friction fit can be sufficiently tight to resist biasing forces provided by the compressed spring 212 that would otherwise urge the carriage 210 in a proximal direction and thereby urge the female cap 102 away from the male cap 104. The friction fit also can provide a fluid-tight seal that can prevent antiseptic 133 from evaporating from an interior of the closed assembly 100 to an exterior environment.

FIGS. 10A and 10B illustrate stages in a method of removing the female cap 102 from the assembly 100. In some embodiments, it can be particularly advantageous to use the separation assists 107 in the removal process. For example, as just discussed, in some instances, the friction-fit engagement and/or fluid-tight seal between the caps 102, 104 can be relatively tight. Moreover, in some instances, a slight vacuum may be present within the assembly 100 and/or may arise within the assembly 100 as the cap 102 is removed from or separated from the cap 104. The separation assists 107 thus can advantageously facilitate removal of the cap 102.

FIG. 10A illustrates the assembly 100 in the pre-use state, with the faces 116a, 199a and 116b, 199b of the surfaces 115, 198 in contact with each other. Each paired set of surfaces constitutes a separation assist 107. In the illustrated embodiment the assembly 100 includes four separation assists 107 rotationally spaced from each other at intervals of approximately 90 degrees. Focusing now on an upper separation assist 107 that includes the faces 116a, 199a, the face 116a can define an angle α (see FIG. 4B) of about 20 degrees. The face 199a of the sleeve 191 is at the same angle, although oppositely directed.

In order to separate the cap 102 from the sleeve 191, the cap 102 can be rotated relative the sleeve 191. In the illustrated embodiment, the cap 102 is rotated clockwise, which can cause the faces 116a, 199a to interact with each other and slide past each other. The cap 102 thus cams relative to the sleeve 191 as the rotational motion is converted into translational movement of the cap 102 away from the sleeve 191, as shown by the arrow in FIG. 10B.

Where the angles α, β (see FIG. 4B) of the surfaces 116a, 116b are identical, the same mechanical advantage may be present whether the cap 102 is rotated in the clockwise or counterclockwise directions. In other embodiments, the separation assists 107 can be configured to aid in separating the cap 102 from the sleeve 191 only when the cap 102 is rotated in one predetermined direction (e.g., either clockwise or counterclockwise). For example, the pair of faces 116a or the pair of faces 116b may define an angle α or β, respectively, of 20 degrees so as to allow separation as shown in FIG. 10B, whereas the other pair of faces 116a, 116b may be at an angle of about 90 degrees (i.e., approximately parallel to or extending through a central axis of the cap 104) so as to prevent rotation and separation of the cap 104. For example, in some embodiments, the faces 116a, 116b may be configured to allow the caps 102, 104 to be rotated only in a direction that would decouple threaded portions of the caps 102, 104, so as to thereby prevent initial or further coupling of the threaded portions of the caps 102, 104 (which would tend to pull the caps 102, 104 into tighter engagement with each other, rather than allow them to separate from each other). In other embodiments, one or more of the faces 116a, 116b may be at larger or smaller angles α, β. For example, one or more of the angles α, β may be no more than about 15, 20, 1, 45, 60, or 75 degrees or no less than about 15, 20, 1, 45, 60, or 75 degrees. Other configurations of the separation assists 107 are also possible. For example, in some embodiments, the complementary surfaces of the flanges 115, 198 can define angles as just described, but the surfaces may be rounded or otherwise non-planar.

Other arrangements of the separation assists 107 are contemplated. For example, in some embodiments, the female cap comprises one or more protrusions and the male cap comprises corresponding recesses. In further embodiments, the assembly 100 may be devoid of the separation assists 107. Moreover, in some instances, a user may be able to separate the caps 102, 104 from each other by pulling primarily or solely in a substantially longitudinal direction (e.g., without rotating the caps 102, 104 relative to each other).

FIGS. 11A-11D illustrate consecutive stages of the male cap 104 being coupled with a medical device 300. In FIG. 11A, the male cap 104 has been removed from the female cap 102. Separation of the female cap 102 from the male cap 104 can reduce and eliminate opposition to the biasing force of the spring 212, such that carriage 200 is urged from the retracted position shown in FIG. 9 to the extended position shown in FIG. 11A. When in the carriage is in the extended position, the male projection 241 can extend proximally beyond an edge of the outer housing 150 so as to be more readily accessible by the device 300. The cap 104 may be said to be in a connection-ready or accessible state when it is in an orientation such as that shown in FIG. 11A, as the inner housing 210 is more readily accessible to the device 300 for connection thereto than it is when the male cap 104 is in the retracted orientation.

The proximal stops 233 of the outer housing 150 can cooperate with the distal stops 256 of the inner housing 210, as discussed above. In some embodiments, once the proximal and distal stops 233, 256 have engaged each other such that relative motion between the outer and inner housings 150, 210 ceases, the spring 212 may continue to provide a biasing force to the inner housing 210. For example, the spring 212 may remain somewhat compressed once the inner housing 210 has been extended. This residual biasing force can resist or oppose movement of the carriage 200 back toward the retracted position when the medical connector 300 is moved distally relative to the cap 104 during coupling, as described below. In other or further embodiments, the sleeve 191 and/or the carriage 200 may comprise a latch system or other suitable mechanism that can prevent distal movement of the carriage 200 relative to the sleeve 191 once the carriage 200 has been moved proximally past a predetermined position. An illustrative example of such a latch system is discussed below with respect to FIG. 17.

The medical device 300 includes a male protrusion 319, which in the illustrated embodiment is a male luer 320. As mentioned above, other arrangements of the male protrusion 319 are also contemplated. A tip 321 of the protrusion 319, can be received within the disinfection chamber 268 prior to contacting the sealing member 190. Stated otherwise, the sealing member 190 can be recessed relative to a proximal end of the inner housing 210 by a distance that is sufficiently great to permit at least a portion of the male luer 320 to be received within the inner housing 210 before the male luer contacts the sealing member 190.

In the illustrated stage of the procedure, the luer 320 has been advanced sufficiently far into the disinfection chamber 268 to contact the sealing member 190 and to form a seal therewith. The connection interface 242 of the inner housing 210 has not yet engaged a connection interface 312 of the medical connector 300 at this stage, and the sealing member 190 is just beginning to move distally within the disinfection chamber 268 so as to break the proximal seal between the sealing member 190 and the shelf 274.

One or more portions of the biasing member 176 (i.e., one or more of the resilient support 177 and the pad 170) may provide a biasing force to the sealing member 190 that is smaller than the biasing force that the spring 212 provides to the carriage 200. Accordingly, distal movement of the sealing member 190 may cause compression of one or more portions of the biasing member 176, so as to break the proximal seal between the sealing member 190 and the shelf 274, but may cause little or no compression of the spring 212. The spring 212 thus may provide a suitable level of resistance to axial forces. In other or further embodiments, such as that described below with respect to FIG. 17, one or more latches may be used, which can ultimately provide a resistive force that permits distal movement of the sealing member 190 upon insertion of a portion of medial connector and/or that otherwise provides a suitable level of resistance to axial forces so as to permit desired operation of the male cap 104.

Figure 11B:
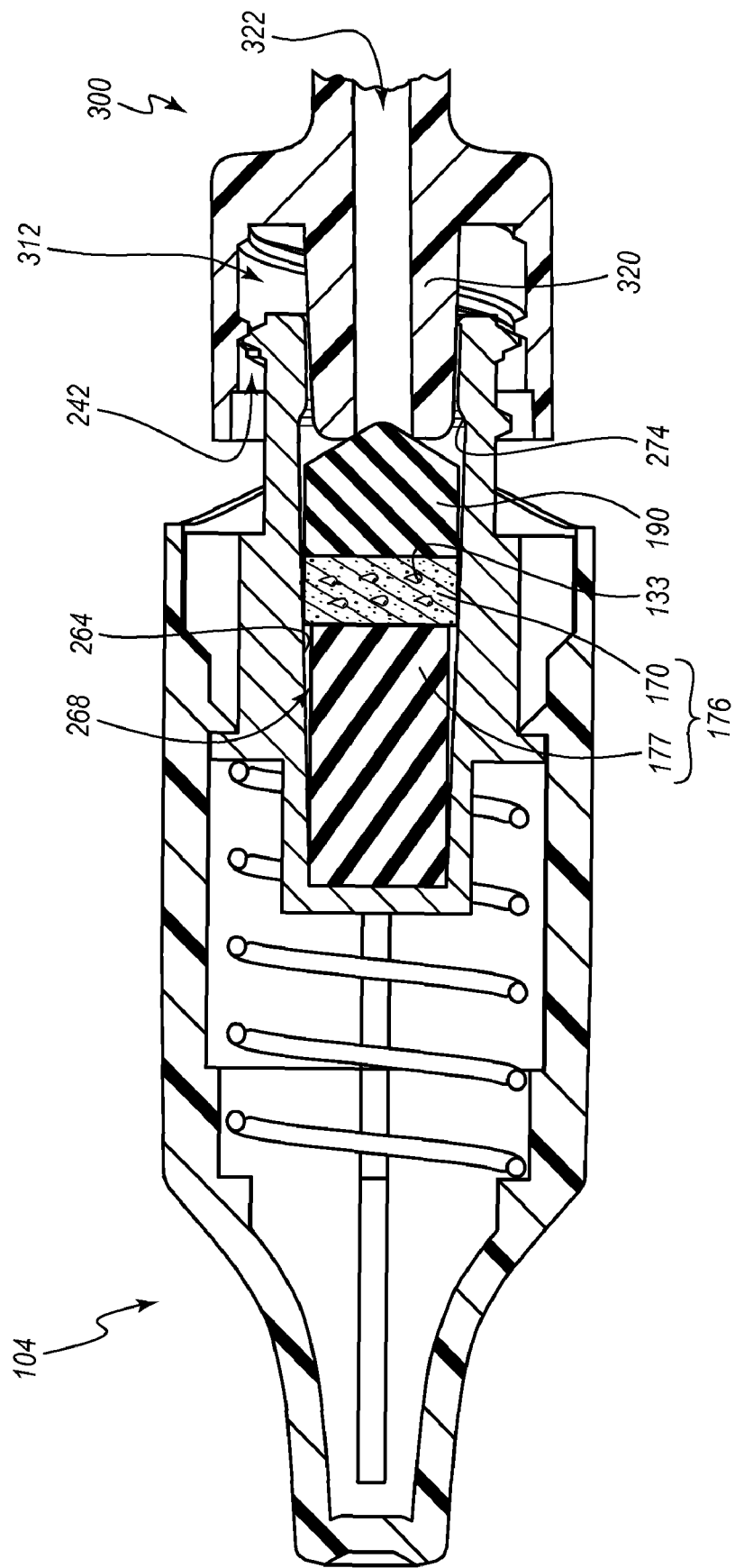

In FIG. 11B, the luer 320 has been advanced slightly further into the disinfection chamber 268, thereby compressing the pad 170 somewhat and forcing antiseptic 133 out of the pad 170. The sealing member 190 can define an outer diameter than is smaller than an inner diameter of this portion of the disinfection chamber 268 such that a fluid path is present about an exterior of the sealing member 190. Stated otherwise, the sealing member 190 has been urged distally to a position where a periphery or outermost perimeter of the sealing member 190 is spaced from the an interior surface of the inner housing 210 such that an opening, spacing, or gap that exists between the sealing member 190 and the interior surface of the inner housing 210. This opening may function as a fluid port.

Antiseptic 133 thus can flow about the sealing member 190 and/or any other portion of an open region that exists between the interior surface of the inner housing 210 and the outer surfaces of the resilient support 177, the pad 170, the sealing member 190, and the luer 320. Further advancement of the luer 320 into the disinfection chamber 268 can cause the antiseptic 133 to fill this open region. However, the antiseptic 133 does not enter into the lumen 322 of the luer 320 due to the seal between the luer 320 and the sealing member 190. Further advancement of the luer 320 into the disinfection chamber 268 also can strengthen the seal between the luer 320 and the sealing member 190 due to the increasing restorative forces that arise as the pad 170 is compressed.

As the pad 170 is softer or more compliant than the resilient support 177, the pad 170 has been compressed to a much greater extent than the resilient support 177 at this stage. Indeed, in some embodiments, the resilient support 177 may compress only slightly or not at all at this stage.

In the illustrated embodiment, the interfaces 242, 312 have just begun coupling with each other at the stage shown in FIG. 11B. The threaded interfaces 242, 312 are configured to be rotated relative to each other for purposes of engagement and disengagement. As previously discussed, the movement constraining members 230, 253 can cooperate with each other to limit or prevent rotation of the inner housing 210 relative to the outer housing 150, which thus can facilitate coupling and/or decoupling of the medical connector 300 to/from the male cap 104. For example, rotation of the housing 150 can directly impart or transmit torque to the inner housing 210 due to the movement constraining members 230, 253, which can provide a natural feel to a user. The handle 137 portion and/or the sleeve 191 portion of the male cap 104 thus can readily serve as a grip for rotationally coupling the male cap 104 to a medical connector. Moreover, in certain embodiments, upon engagement of the threaded interfaces 242, 312 with each other, rotational motion of the medical connector 300 relative to the male cap 104 can draw the luer 320 into the disinfection chamber 268 without giving rise to any or significant longitudinally directed forces that would tend to urge the carriage 200 distally toward the retracted position. The handle 137 portion of the male cap 104 can conveniently be used for imparting or opposing rotational movement relative to the medical connector 300.

Figure 11C:
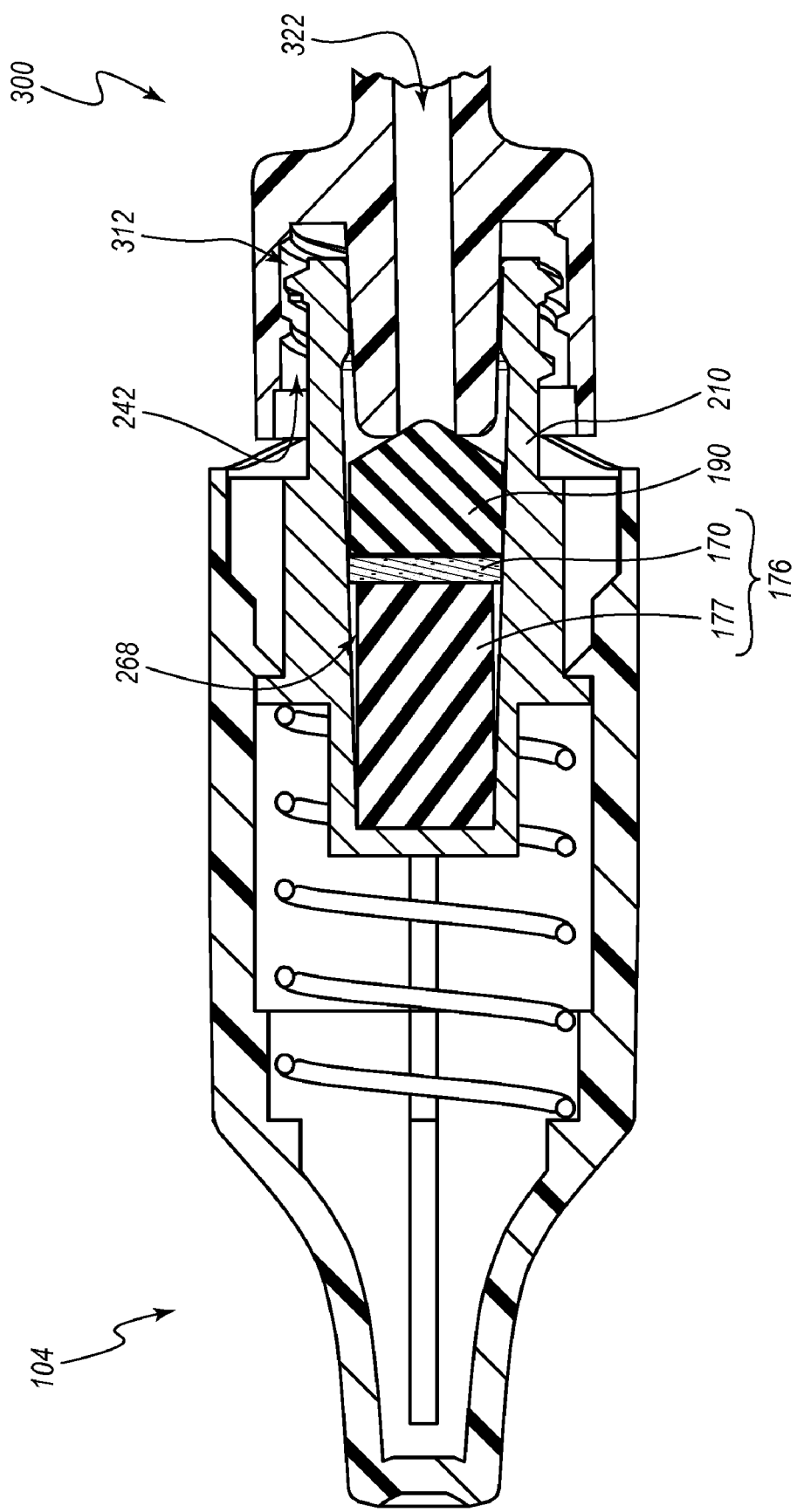

In FIG. 11C, the luer 320 has been advanced even further into the disinfection chamber 268, thereby compressing the pad 170 to a greater extent and forcing additional antiseptic 133 into the interior regions of the disinfection chamber 268. In the illustrated embodiment, the resilient support 177 is shown as having been slightly compressed relative to its configuration in the stage shown in FIG. 66C, whereas the pad 170 has been nearly completely compressed, such that all or nearly all of the antiseptic 133 has been forced therefrom. Cooperation between the connection interfaces 142, 312 can facilitate compression of the pad 170 and/or the resilient support 177.

Although the outer surface of the luer 320 appears to be nearly parallel to and in contact with the luer-tapered surface 272 of the interior surface of the inner housing 210, a fluid-tight seal may not have formed yet in this area. Accordingly, the antiseptic 133 may be permitted to cover the portion of the luer 320 that is within the chamber 268, while in some embodiments, a small portion of antiseptic 133 may also be permitted to exit from the disinfection chamber 268. The portion of the luer 320 that is within the disinfection chamber 268 thus may contact the antiseptic 133 so as to be disinfected thereby.

Figure 11D:
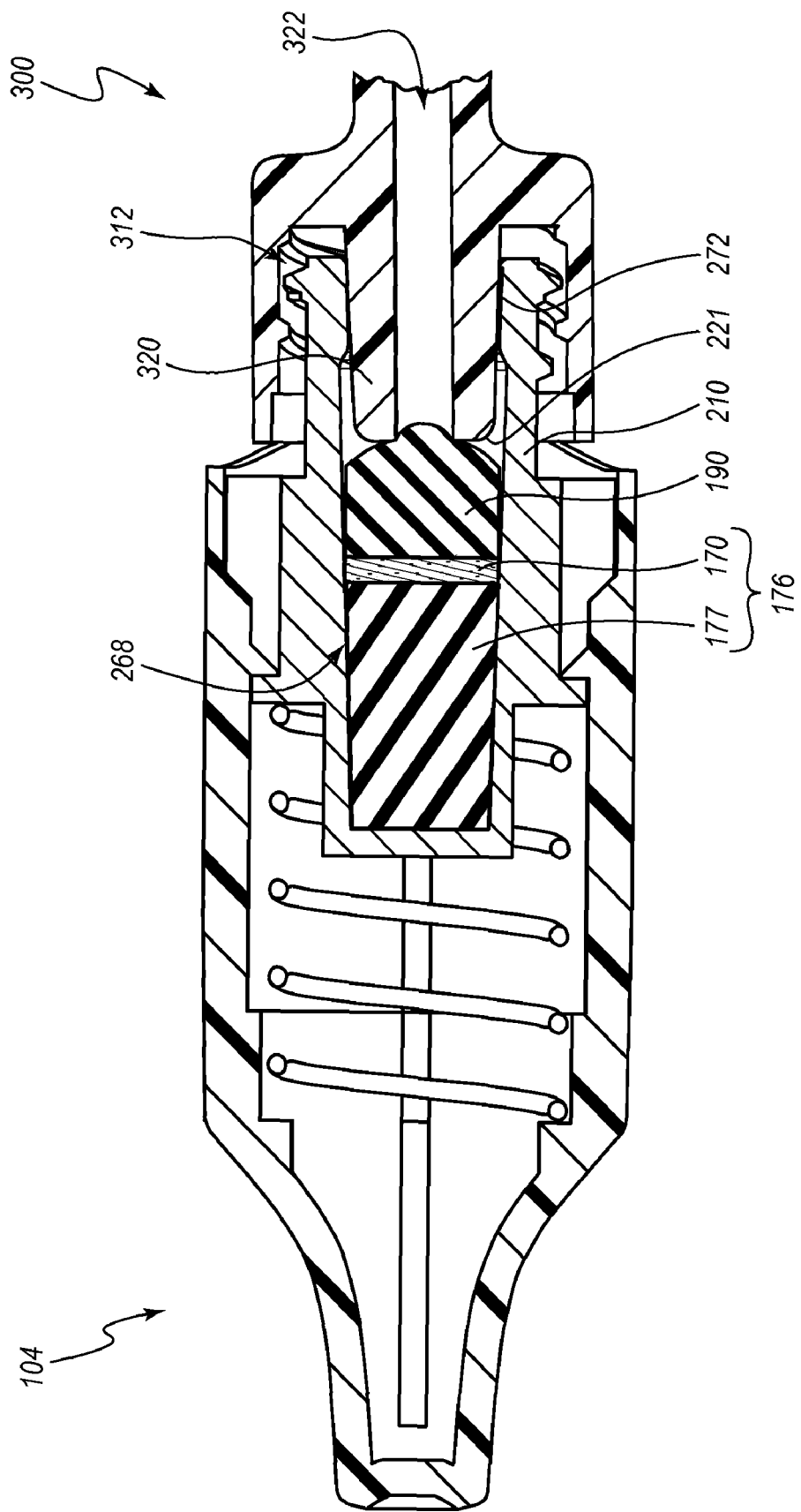

FIG. 11D illustrates a final or fully coupled stage, or an end-of-stroke orientation, in which the luer 320 has been advanced even further into the disinfection chamber 268 such that the luer 320 forms a seal with the luer-tapered surface 272 of the inner housing 210. Antiseptic 133 can be retained in all open portions of the disinfection chamber 268 that are between the seal formed by the luer 320 and the sealing member 190 and the seal formed by the luer 320 and the inner housing 210. In the illustrated embodiment, a relatively large portion of the luer 320, which includes all or most of the tip 321, is in continual contact with the portion of the antiseptic 133 thus retained. This portion of the luer 320 can be bathed by the antiseptic 133 and disinfected thereby. In other embodiments, larger portions of the luer 320 can be bathed.

The deformable nature of the resilient support 177 can allow for distal movement of the pad 170, even after the pad 170 has been fully compressed. Such an arrangement can allow for a range of acceptable lengths and diameters for the luer 320. For example, shorter luers 320 than that illustrated in the drawings may still be able to fully compress the pad 170 so as to expel all antiseptic therefrom.

In other embodiments, the medical connector 300 may include a male protrusion other than a luer 320, such as a male protrusion that is shaped substantially as a cylinder or in some other configuration, such as a taper having dimensions other than those used for luer systems. In some embodiments, the surface 272 may be shaped complementarily to the outer surface of such protrusions so as to for a seal therewith. In still other embodiments, the inner housing 210 may not form a seal with the protrusion.

When the luer 320 is removed from the chamber 268, the restoration forces of the pad 170 and/or the resilient support 177 (i.e., the biasing member 176) can maintain the seal between the luer 320 and the sealing member 190, which can prevent antiseptic from entering into the lumen 322 of the luer 320.

Figure 12:
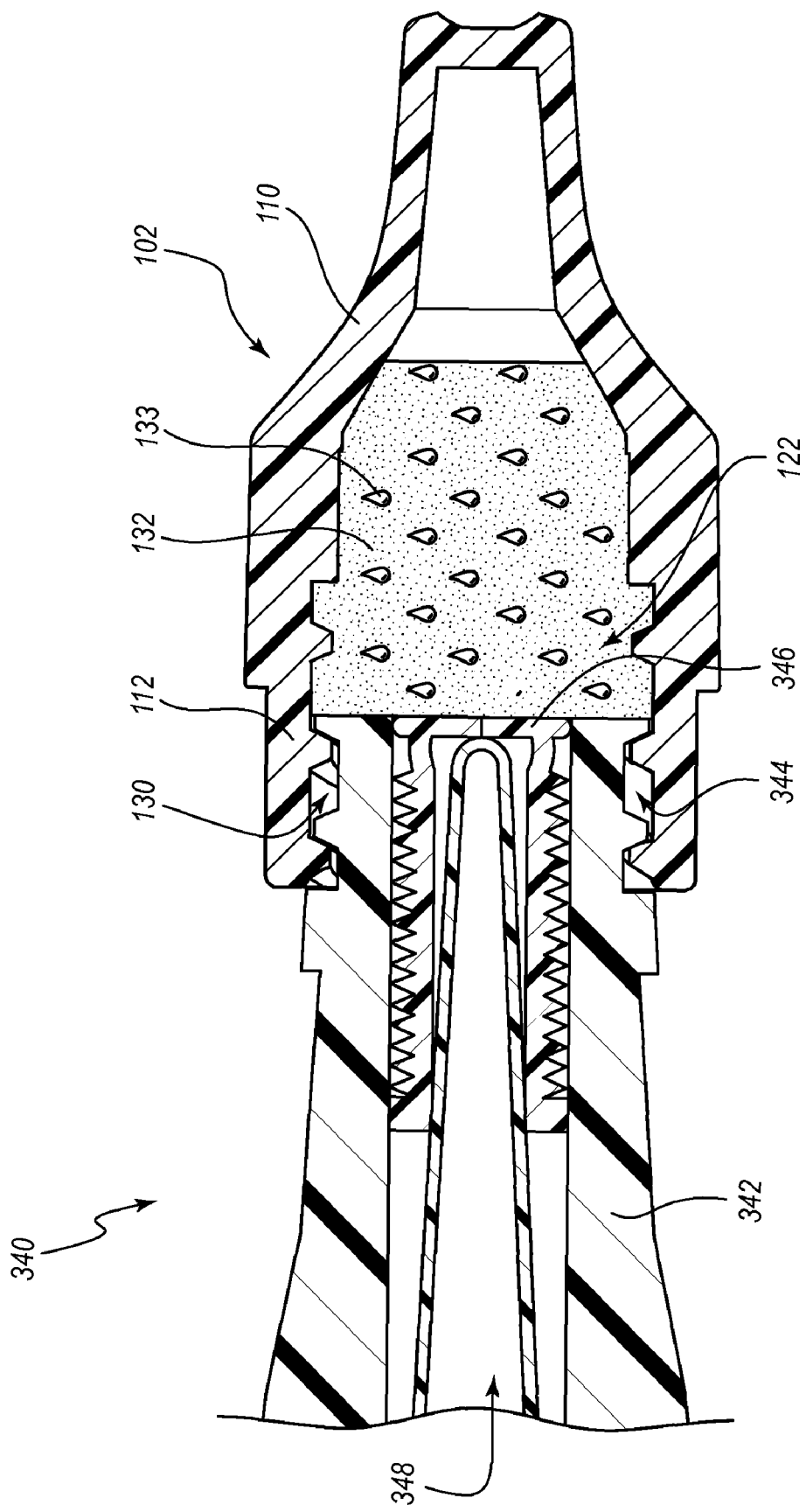
FIG. 12 is a cross-sectional view of the female cap of FIG. 1 coupled with an embodiment of a needleless injection site.
Figure 13:
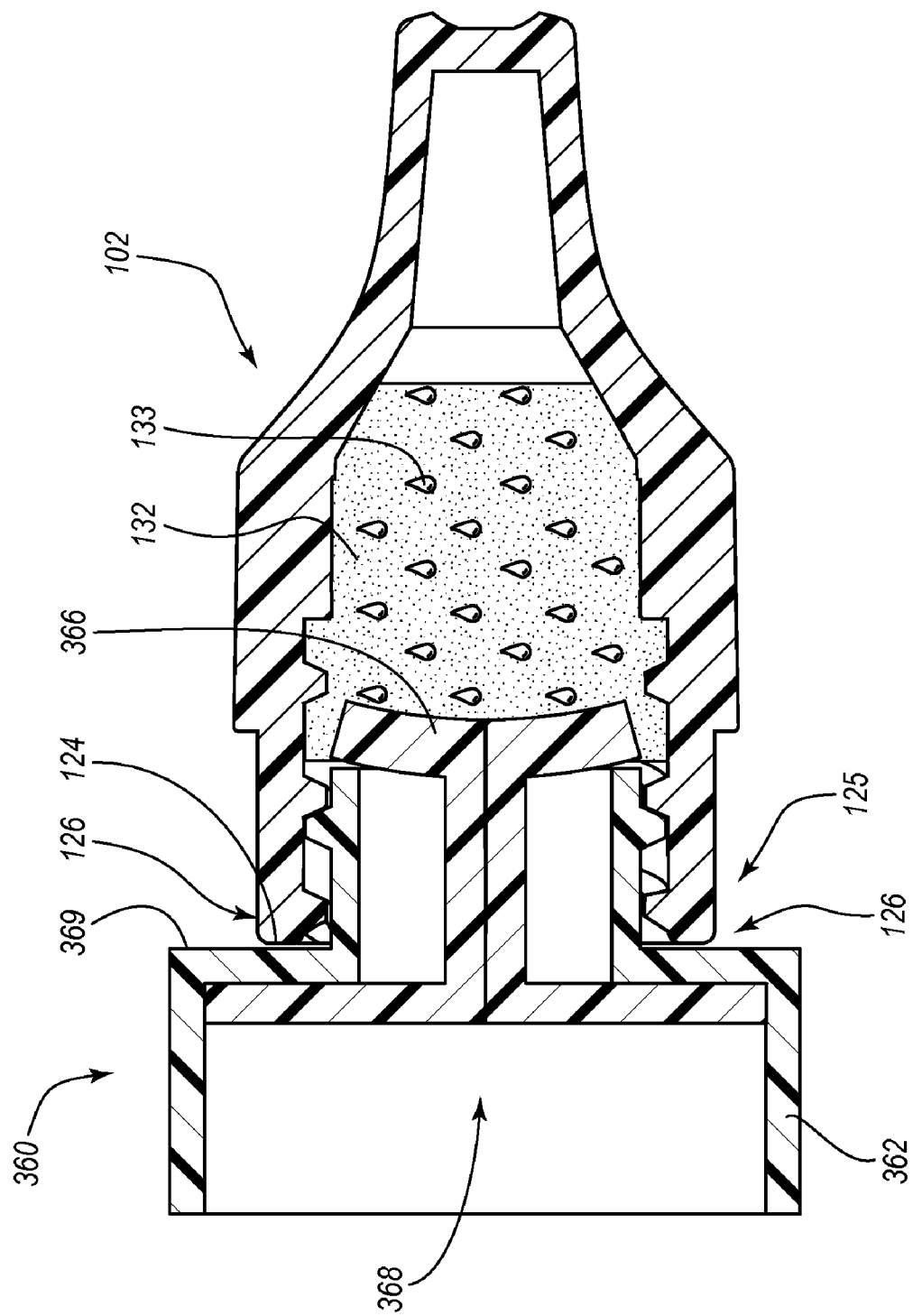
FIG. 13 is a cross-sectional view of the female cap of FIG. 1 coupled with another embodiment of a needleless injection site.
Figure 14:
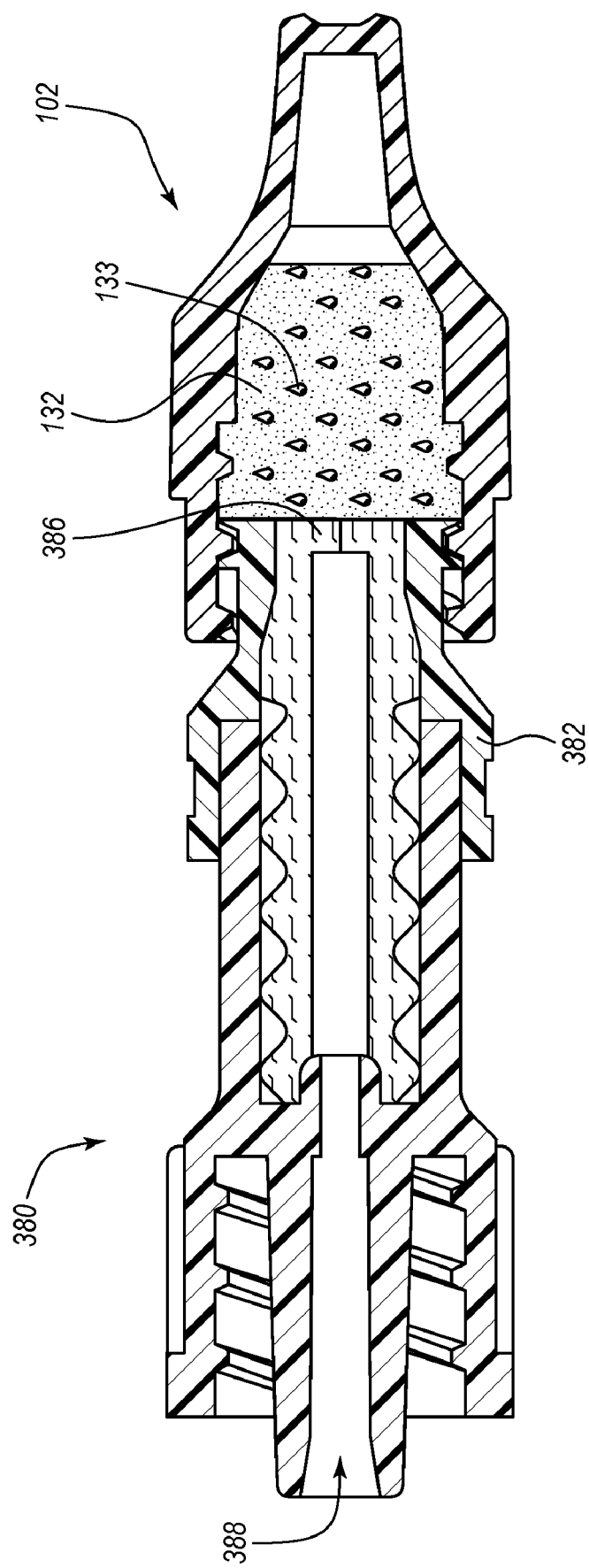
FIG. 14 is a cross-sectional view of the female cap of FIG. 1 coupled with another embodiment of a needleless injection site.

Each of FIGS. 12-14 illustrates the female cap 102 coupled with a separate needleless injection site 340, 360, 380. The cap 102 can be versatile so as to couple with a variety of different types of medical connectors in a secure fashion that disinfects each type of medical connector. As can be seen in each of FIGS. 12-14, coupling of the needleless injection sites 340, 360, 380 with the cap 102 can effect compression of one end of the pad 132. This compression, along with rotation of the needleless injection site 340, 360, 380 can effect rubbing, swabbing, or scrubbing of the needleless injection site and disinfection thereof via the antiseptic 133.

With reference to FIG. 12, the needleless injection site 340 can comprise a Clave® port available from ICU Medical, Inc. The needleless injection site 340 can include a housing 342 that defines a connection interface 344. The needleless injection site 340 can further include an elastomeric seal 346, which is shown in a closed configuration in which fluid access is not permitted into a fluid passageway 348. Small crevices can exist between the housing 342 and the elastomeric seal 346 at an end of the needleless injection site 340 that is inserted into disinfection chamber 1922. As the connection interface 344 cooperates with the connection interface 1930 defined by the sidewall 112 to draw the tip of the needleless injection site 340 into the disinfection chamber 122, the pad 132 can be compressed so as to generally conform to the crevices. Compression of the pad 132 likewise can expel antiseptic 133, which, in some instances, can fill in portions of the crevices that the pad 132 may not be able to contact directly. As the pad 132 is compressed, the seal 346 can remain closed so as to prevent antiseptic 133 from entering the fluid passageway 348.

With reference to FIG. 13, the needleless injection site 360 can comprise a Q-Syte® port available from Becton, Dickinson and Company. The needleless injection site 360 can include a housing 362 and an elastomeric seal 366, which is shown in a closed configuration in which fluid access is not permitted into a fluid passageway 368. As with the needleless injection site 340, small crevices can exist between the housing 362 and the elastomeric seal 366. However, the crevices can exist at a side portion of the needleless injection site 360, rather than at its tip. Nevertheless, as the needleless injection site 360 is advanced into the cap 102, the pad 132 can be compressed so as to generally conform to these differently shaped crevices. Compression of the pad 132 likewise can expel antiseptic 133, which, in some instances, can fill in portions of the crevices that the pad 132 may not be able to contact directly. The seal 366 can be maintained in the closed position during the coupling procedure, so as to prevent any of the antiseptic 133 from entering the fluid passageway 368.

With reference to FIG. 14, the needleless injection site 380 can comprise a SmartSite® port available from Cardinal Health, Inc. The needleless injection site 380 can include a housing 382 and an elastomeric seal 386, which is shown in a closed configuration in which fluid access is not permitted into a fluid passageway 388. As with the needleless injection sites 340, 360, small crevices can exist between the housing 382 and the elastomeric seal 386. However, these crevices can be in yet different positions than those of the needleless injection sites 340, 360. Nevertheless, as the needleless injection site 380 is advanced into the cap 1102, the pad 132 can be compressed so as to generally conform to these differently shaped crevices. Compression of the pad 132 likewise can expel antiseptic 133.

Each of the needleless injection sites 340, 360, 380 may advance into the cap 102 by different amounts. The cap 102 thus can be adaptable and versatile. Additional, non-limiting examples of needleless injection sites with which the cap 102 can selectively couple include the Clearlink® Site available from Baxter and the InVision-Plus® available from Rymed.

As shown in FIG. 13, in some arrangements, a portion of the seal inhibitor 125 can contact an outwardly projecting surface 369 of a needleless injection site 360. In particular, the proximal end 124 of the cap 102 can contact the surface 369 at two separate contact regions 126 when the cap 102 is fully coupled with the needleless injection site 360. In the venting regions 127 (not shown in FIG. 13, see FIGS. 4A and 4B), the proximal end 124 of the cap 102 can be spaced from the surface 369. Such an arrangement can allow venting of antiseptic from the disinfecting chamber 122 through the venting regions 127 into the surrounding environment.

Figure 15:
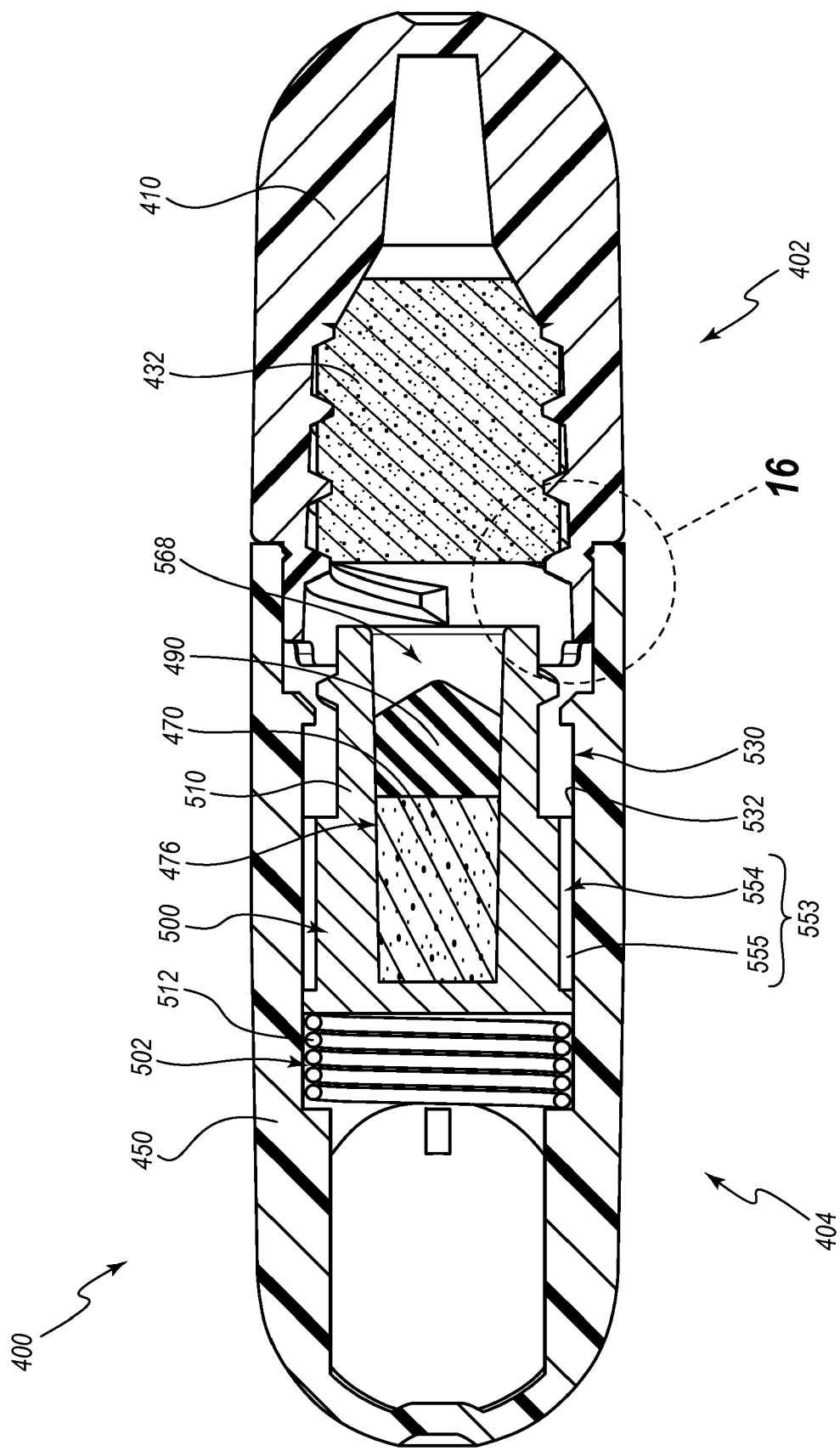
FIG. 15 is a cross-sectional view of another embodiment of an assembly that includes an embodiment of a male cap and an embodiment of a female cap that are coupled with each other in a closed or pre-use configuration.
Figure 16:
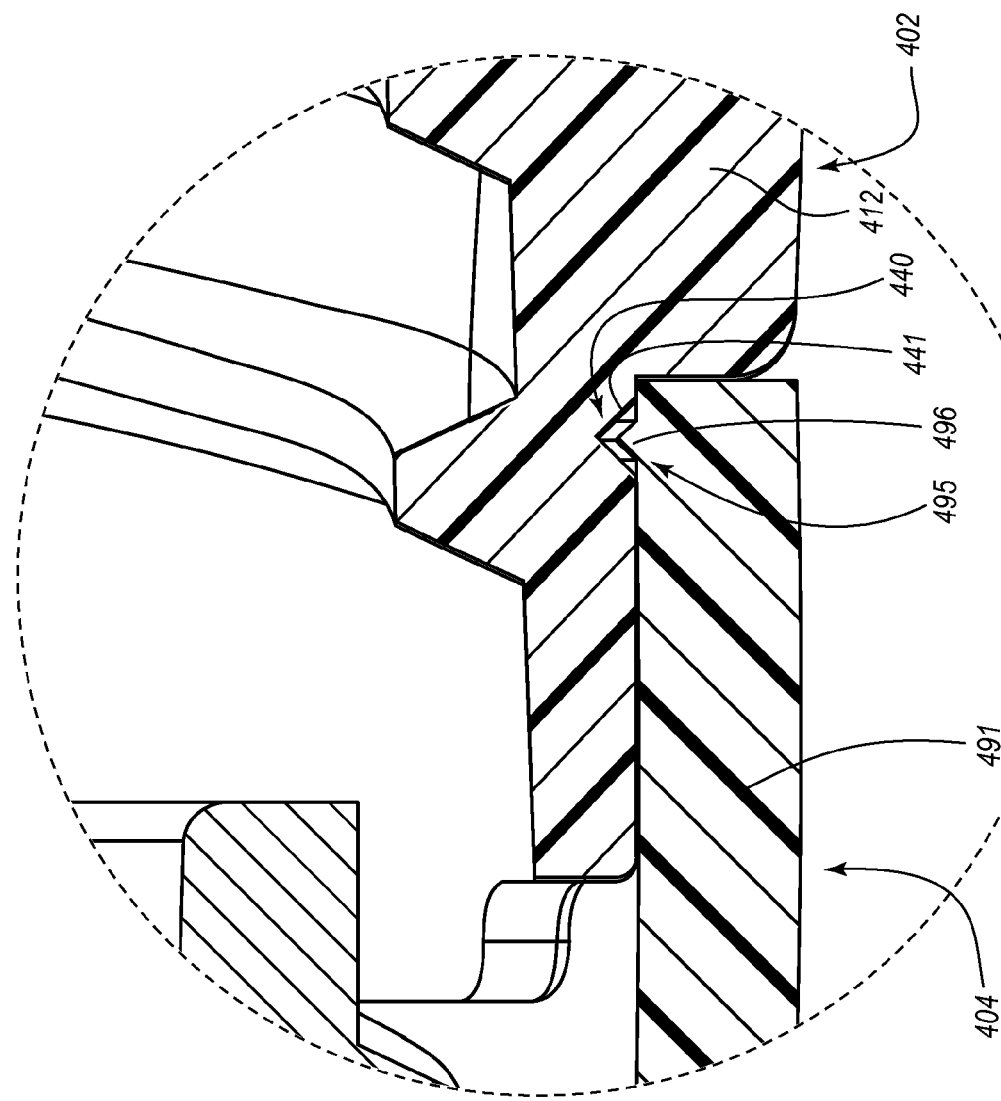
FIG. 16 is an expanded view of the cross-sectional view shown in FIG. 15.

FIGS. 15 and 16 illustrate another embodiment of an assembly 400 that includes an embodiment of a female cap 402 and an embodiment of a male cap 404, which can resemble the assembly 100 and caps 102, 104 described above in certain respects. Accordingly, like features are designated with like reference numerals, with the leading digits "1" incremented to "4," and the leading digit "2" incremented to "5." Relevant disclosure set forth above regarding similarly identified features thus may not be repeated hereafter. Moreover, specific features of the assembly 400 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the assembly 400. Any suitable combination of the features and variations of the same described with respect to the assembly 100 can be employed with the assembly 400, and vice versa. Such disclosure methods apply to additional embodiments disclosed hereafter, such as those shown in each of FIGS. 17, 18, 19, and 20.

The female cap 402 includes a housing 410 that contains a pad 432. The housing 410 includes a sidewall 412 that defines a connection interface 440. The male cap 404 includes an outer housing 450 that includes a telescoping carriage 500 therein. The outer housing 450 includes a sleeve 491 that defines a connection interface 495. The connection interface 495 of the sleeve 491 is configured to cooperate with the connection interface 440 of the sidewall 412 to couple the male cap 404 to the female cap 402 so as to maintain the assembly 400 in the pre-use configuration. The coupled connection interfaces 440, 495 may form a fluid-tight seal, such as described above.

In the illustrated embodiment, the connection interfaces 495 comprises an annular projection 496 that extends radially inwardly, and the connection interfaces 440 comprise a complementary annular recess 441 that also extends radially inwardly. Each of the projection 496 and the recess 441 can extend about at least a portion of the respective caps 402, 404 and can function as a snap-fit connection interface. In other embodiments, the connection interface 495 may instead comprise a recess and the connection interface 440 may instead comprise a complementary projection. Other suitable connection interfaces are also contemplated.

An inner housing 510 of the carriage 500 can be somewhat shorter than the inner housing 210 described above. For example, the inner housing 510 may be devoid of a distal extension portion (such as the distal extension 258). Correspondingly, a disinfecting chamber 568 defined by the inner housing 510 may be shorter than the disinfecting chamber 268.

A biasing member 476 may comprise only a single piece, which in the illustrated embodiment is a resilient pad 470 that comprises an antiseptic therein. A sealing member 490 can be attached to or otherwise positioned at a proximal end of the pad 470, and may function in a manner similar to the sealing member 190 described above.

The outer housing 450 can include one or more movement constraining members 530 that are configured to cooperate with one or more movement constraining members 553 of the inner housing 510 in manners such as described above. The movement constraining members 530 of the outer housing 450 can comprise splines 532 that are similar to the splines 232 describe above. However, in the illustrated embodiment, the splines 532 do not include stops (such as the stops 232) at the proximal ends thereof. The movement constraining members 553 of the inner housing 510 can comprise channels 554 that are defined by sidewalls 555. However, the movement channels 554 may not include stops (such as the stops 256) at the distal ends thereof. Accordingly, the movement constraining members 530, 553 may be configured primarily to limit rotational movement of the inner housing 510 relative to the outer housing 450, without limiting longitudinal (e.g., translational) movement between the inner and outer housings 510, 450.

In some embodiments, movement of the carriage 510 in the longitudinal direction may be controlled or limited by a biasing member 502. For example, the biasing member 502 can comprise a spring 512 that is attached to a distal end of the carriage 512. The compressed spring 512 can move the carriage 500 from the retracted position shown in FIG. 15 to an extended position (such as that shown in FIG. 11A). When the carriage 500 is in the extended position, the spring 512 may be in a natural or uncompressed state, such that the spring 512 naturally maintains the carriage 500 in the extended position. Any further proximal movement of the carriage 500 thus would give rise to a restorative or biasing force in the spring 512 that would tend to move the carriage 500 back to the extended position, which corresponds with the equilibrium position of the spring 512. In other or further embodiments, as discussed further below, one or more of the inner and outer housings 510, 450 can comprise latching or locking features that secure the carriage 500 in the extended position once it has been moved thereto.

Any suitable arrangement of antiseptic, pads, and/or sealing members may be used within the disinfecting chamber 568. Examples of various suitable arrangements can be found in U.S. patent application Ser. No. 12/917,336, titled DISINFECTING CAPS AND SYSTEMS AND ASSOCIATED METHODS, filed Nov. 1, 2010, the entire contents of which were previously incorporated by reference herein.

Figure 17:
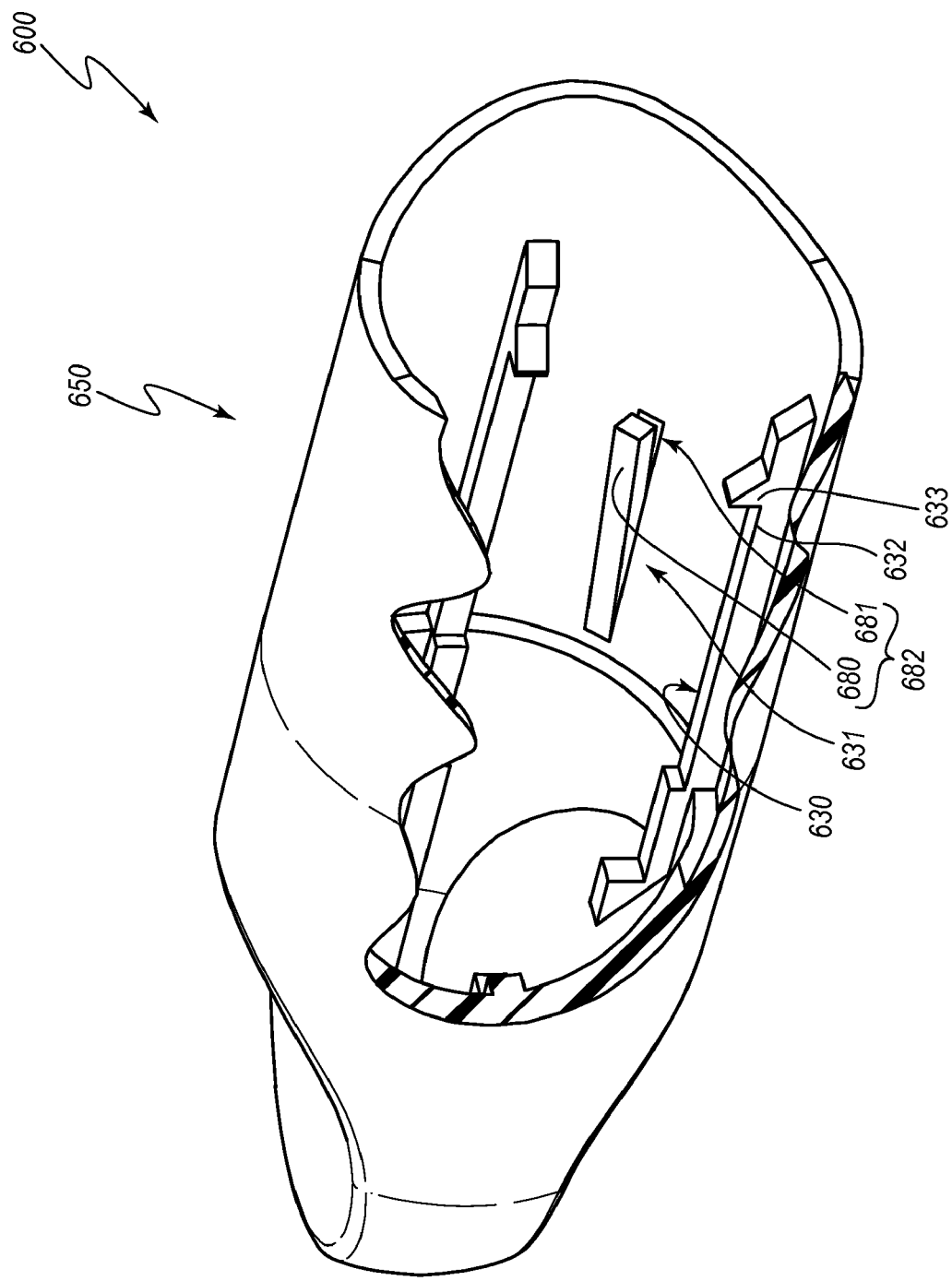
FIG. 17 is a cutaway perspective view of an embodiment of a housing portion of another embodiment of a male cap.

FIG. 17 illustrates an embodiment of an outer housing 650 that can be used in a male cap, which may be used with an assembly 600. The assembly 600 can resemble any of the assemblies discussed above. The outer housing 650 can particularly resemble the outer housing 150, and can include one or more movement constraining members 630 such as the movement constraining members 230 described above. For example, the movement constraining members 630 can include splines 632 that include proximal stops 633, and the stops can be configured to prevent a carriage 200, 500 from being fully extracted or urged from the outer housing 650.

The assembly 600 can further include an additional movement constraining member 631 that is configured to maintain a carriage 200, 500 in the extended position, or stated otherwise, that is configured to prevent a carriage 200, 500 from being moved distally past a predetermined position once the carriage 200, 500 has been moved from the retracted position to the extended position. Any suitable locking, latching, or retaining system may be used for the movement constraining member 631. For example, in the illustrated embodiment, the outer housing 650 includes resilient arms 680 that are configured to move into a recess 681. Only one arm 680/recess 681 system is shown in FIG. 17, but additional such systems may be distributed about the outer housing 650. The additional systems may be at the same longitudinal position, but angularly spaced about the housing 650. The resilient arms 680 naturally angle inwardly toward an axial center of the outer housing 650 in a proximal direction. Movement of the carriage 200, 500 in a proximal direction can urge the resilient arms radially outwardly into the recesses 681. Once the carriage 200, 500 has passed the resilient arms 680, the arms 680 can return to their natural inwardly projecting orientation, and proximal surfaces of the arms can contact one or more distal surfaces of the carriage 200, 500 (e.g., the distal surface 257 shown in FIG. 8) so as to prevent the carriage 200, 500 from thereafter moving distally within the outer housing 650.

The resilient arm 680/recess 681 pair may be referred to as a latching system 682. Any suitable arrangement of the latching system is contemplated, and the system may include detents or other locking features. In some embodiments, a biasing member 202 may include at least a portion of the latching system 682. For example, in some embodiments, the biasing member 202 may include the resilient arm 680 or another suitable locking feature that is forced into the recess 681 once the biasing member 202 has been moved proximally to a predetermined position.

In the illustrated embodiment, the movement constraining members 630, 631 are separate from each other. In other embodiments, they may be integral to each other. For example, in some embodiments, the resilient arm 680 may be incorporated into a spline 632. In other embodiments, the spline 632 may include an additional stop, similar to the stop 633. The additional stop may be at a longitudinal position similar to that of the arm 680 shown in FIG. 17. The stop may be configured to allow the carriage 200, 500 to pass by it in the proximal direction so as to move from the retracted to the extended position, but may be configured to prevent the carriage 200, 500 from moving distally past the stop thereafter. The stop may comprise a detent or any other suitable mechanism.

Figure 18:
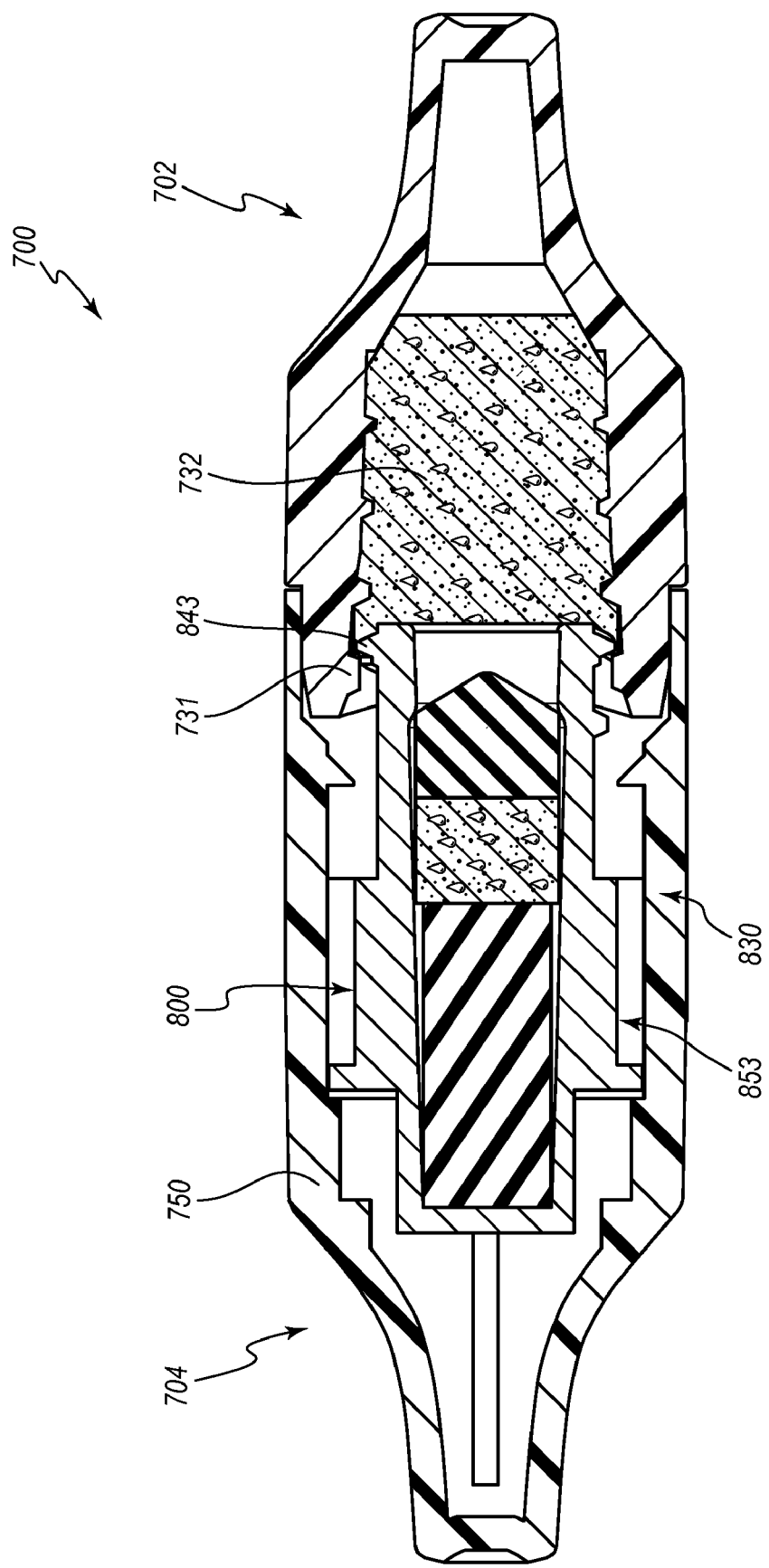
FIG. 18 is a cross-sectional view of another embodiment of an assembly that includes an embodiment of a male cap coupled with an embodiment of a female cap.

FIG. 18 illustrates another embodiment of an assembly 700 that includes an embodiment of a female cap 702 and an embodiment of a male cap 704. The assembly 700 can particularly resemble the assembly 100, but can be devoid of a biasing member. In the illustrated embodiment, a selective engagement is established between a carriage 800 and the female cap 702 such that when the male and female caps 704, 702 are separated for use, the carriage 800 is drawn by this selective engagement from the retracted position to the extended position. Once the carriage 800 has been drawn to the extended position, the selective engagement can be broken.

In the illustrated embodiment, the selective engagement between the female cap 702 and the carriage 800 may comprise an interfacing or interlocking of threads 731 of the female cap 702 and the threads 843 of the carriage 800. For example, rather than mere contact between proximal ends of the threads 131, 243, such as shown in FIG. 9, so as to maintain the carriage 200 in the retracted position, a larger portion of the proximal portions of the threads 731, 843 that are shown in FIG. 18 may be engaged with each other so as to both maintain the carriage 800 in the retracted position and draw the carriage 800 from the retraced position when the female cap 702 is pulled away from an outer housing 750 of the male cap 704. Once the female cap 704 has thus translated the carriage 800 to the desired position, the female cap 702 may be rotated relative to the carriage 800 (and, due to motion constraining members 830, 853, relative to the outer housing 750 as well) so as to disengage the threading 731, 843 and fully separate the female cap 702 from the male cap 704.

In the illustrated embodiment, a proximal end of the carriage 800 compresses a proximal end of a pad 732 that is within the female cap 702 when the assembly 700 is in the pre-use state. In other embodiments, the proximal end of the carriage 800 may be spaced from the pad 732 when the assembly is in the pre-use state so as not to compress the pad 732.

In other or further embodiments, selective engagement between the female cap 702 and the carriage 800 can be effected by snap fitting, friction fitting, heat stake, and/or other suitable approaches. In some embodiments, the carriage 800 may be retained in the extended position, once it has been drawn thereto, by locks, detents, or other suitable features, as described above with respect to FIG. 17. For example, in some embodiments, the carriage 800 and/or the outer housing 750 may comprise a latch such that, once the carriage has been moved to the proximal position, the latch prevents distal motion of the carriage relative to the outer housing 150.

Figure 19:
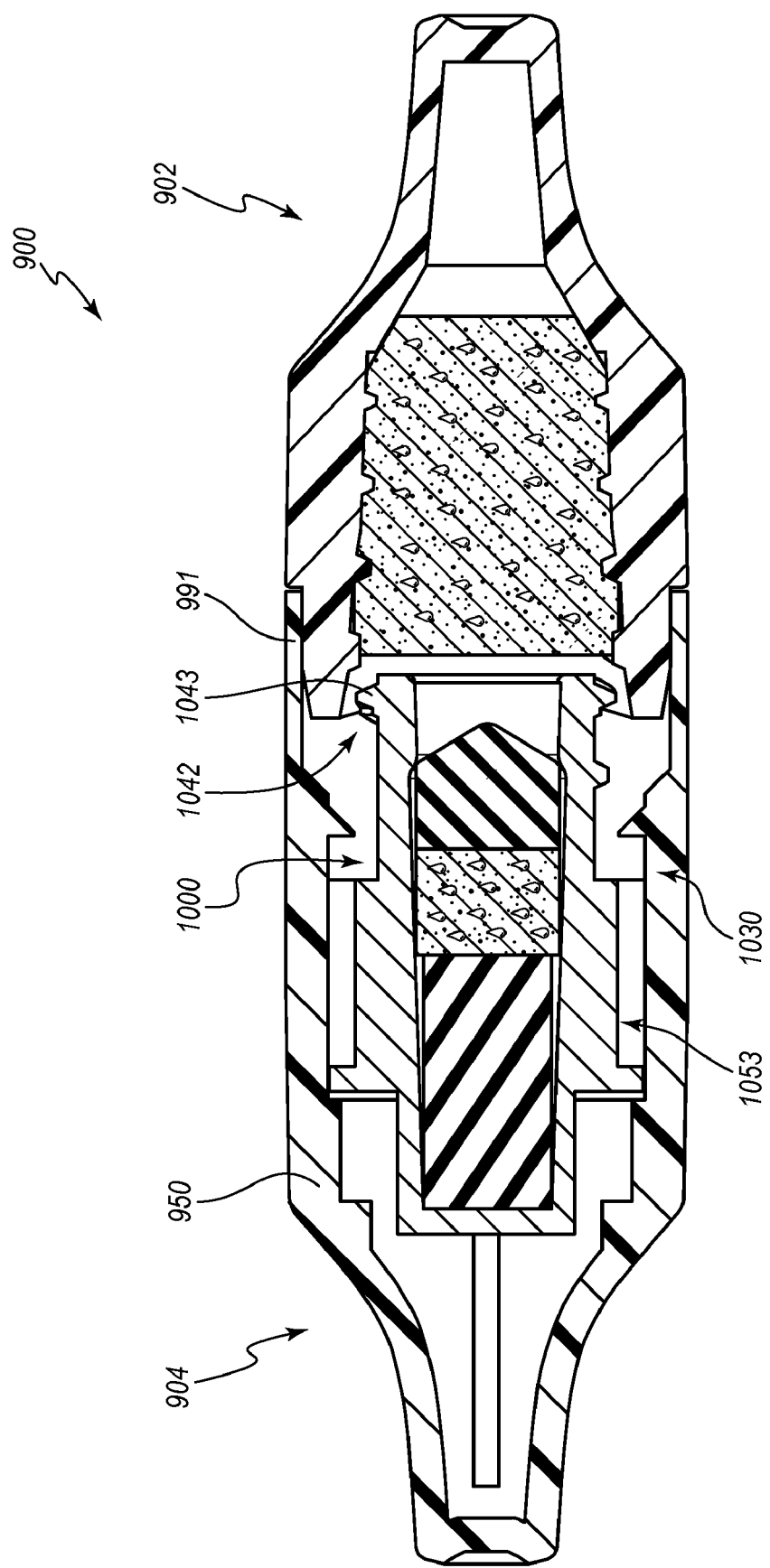
FIG. 19 is a cross-sectional view of another embodiment of an assembly that includes an embodiment of a male cap coupled with an embodiment of a female cap.

FIG. 19 illustrates another embodiment of an assembly 900 that includes an embodiment of a female cap 902 and an embodiment of a male cap 904. As with the assembly 700, the assembly 900 can be devoid of a biasing member that is configured to move a carriage 1000 from a retracted position to an extended position. Unlike the assembly 700, the assembly 900 may further be devoid of features that couple the female cap 902 to the carriage 1000 so as to move the carriage 1000 from the retracted position to the extended position. Coupling of a medical connector (such as the connector 300 discussed above) to a connection interface 1042 of the carriage 1000 may draw the carriage 1000 from the retracted position to the extended position.

For example, in some embodiments, a sleeve portion 991 of an outer housing 950 of the male cap 904 can be sufficiently shallow to permit at least a portion of the connection interface 312 of the connector 300 (see FIG. 11A) to engage a proximal portion of the connection interface 1042. Tightening of the connector 300 onto the carriage 1000, such as via rotation of the connector 300 relative to the carriage 1000, can draw the carriage 1000 from the retracted position to the extended position. In particular, the carriage 1000 can translate relative to the outer housing as the threaded connection interface 312 is advanced onto threads 1043 of the connection interface 1042. In some embodiments, a set of movement constraining members 1030, 1053 can prevent the carriage 1000 from rotating relative to the outer housing 950 and can ensure that the only or primary relative movement between the outer housing 950 and the carriage 1000 is translational in a longitudinal direction.

Figure 20:
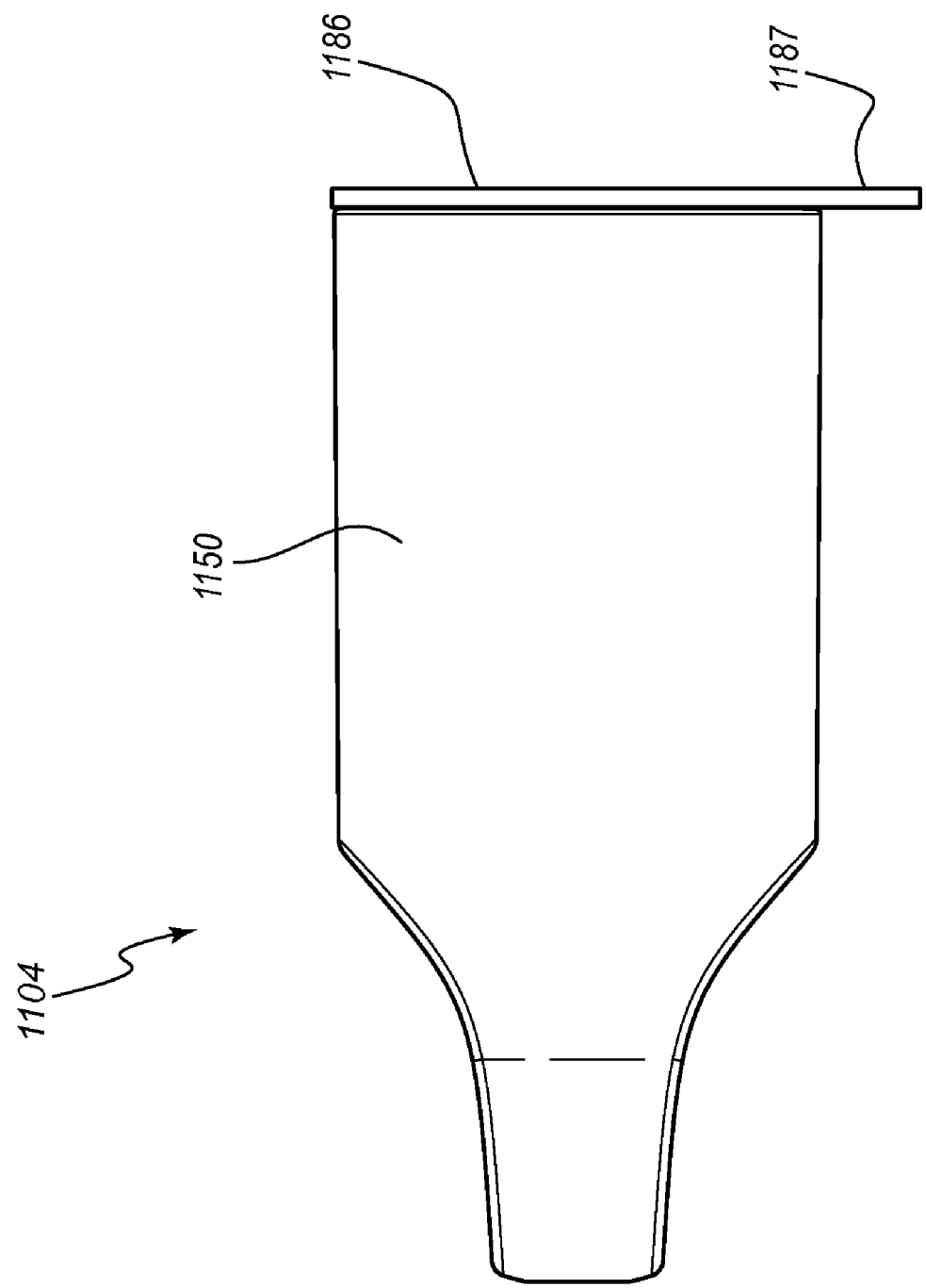
FIG. 20 is a side elevation view of another embodiment of a male cap.

In some embodiments, a male cap can be packaged independently of any female caps when in a pre-use state, such that it may not be part of an assembly. For example, as shown in FIG. 20, in some embodiments, a proximal end of a male cap 1104 may be substantially flat or planar (e.g., devoid of the protrusions 197), and a removable cover 1186 may be secured to an outer housing 1150 of the cap 1104 in any suitable manner, such as, for example, via an adhesive. Preferably, the cover 1186 can be readily removed by a practitioner. The cover 1186 may include a graspable tab 1187 to aid in the removal thereof. The adhesive may be sufficiently strong to maintain the cover hermetically sealed about the proximal end of the outer housing 1150, and the cover and adhesive may be sufficiently strong to counter the biasing force of a biasing member (e.g., the biasing member 202) so as to maintain an inner housing in the retracted position. The removable cover 1186 can be formed of any suitable material, such as, for example, an impervious pliable material (e.g., foil, plastic, metallized-surface mylar). Examples of suitable covers are illustrated in U.S. patent application Ser. No. 12/917,336, titled DISINFECTING CAPS AND SYSTEMS AND ASSOCIATED METHODS, filed Nov. 1, 2010.

In some embodiments, the female caps 102, 402, 702, 902, which can be configured for use with medical connectors, may be replaced with caps having a sole or primary purpose of covering the male caps 104, 404, 704, 904 prior to use so as to maintain the sterility of the male caps, so as to prevent evaporative loss from the male caps, and/or so as to maintain the carriage portions of the male caps in the retracted position. Additionally, as previously discussed with respect to the assembly 100, in some embodiments, cooperation between the sealing member 190 and the inner housing 210 can form a seal that is sufficient to prevent evaporative loss from the male cap 104.

The caps described herein, and components thereof, can be formed of, or coated with various colored materials or coatings. In some embodiments, the caps each include the same color. In other embodiments, the caps include different colors. Coloring the caps can, in some instances, provide advantages, such as ready identification of the type of cap, ready matching of a particularly colored cap with a particular type of medical connector, and the like.

The foregoing disclosure recites various embodiments that include caps that are configured to disinfect medical connectors. Certain of such caps can include an outer housing and an inner housing disposed within the outer housing. Illustrative examples of means for transitioning the inner housing from a retracted position to an extended position relative to the outer housing include the biasing members 202, 502, the threading 731, 843, and the connection interface 1042. Illustrative examples of means for constraining movement of the inner housing relative to the outer housing include the movement constraining members 230, 253, 530, 553, 630, 631, 830, 853, 1030, 1053.

It will be understood by those having skill in the art that many changes may be made to the details of the above-described embodiments without departing from the underlying principles presented herein. For example, any suitable combination of features of the various embodiments of assemblies described above is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Recitation in the claims of the term "first" with respect to a feature or element does not necessarily imply the existence of a second or additional such feature or element. Elements recited in means-plus-function format are intended to be construed in accordance with 35 U.S.C. §112¶6. It will be apparent to those having skill in the art that changes may be made to the details of the above-described embodiments without departing from the underlying principles of the invention.

What is claimed is:

1. A cap configured to disinfect a medical connector, the cap comprising:
   an outer housing that defines a proximal end, a distal end, and a cavity that extends from the proximal end toward the distal end; and
   an inner housing disposed within the outer housing, the inner housing comprising a connection interface that is configured to connect the inner housing to a medical connector, the inner housing defining a chamber having therein an antiseptic, a sealing member and a first biasing member, wherein the sealing member is configured to form a seal with a portion of a medical connector that is inserted into the chamber, and wherein the first biasing member is configured to urge the sealing member in a proximal direction toward an open end of the chamber;
   a second biasing member that is coupled with each of the outer and inner housings, wherein the second biasing member is configured to bias the inner housing toward the extended position:
   wherein the cap is configured to transition from a pre-use state, in which the inner housing is in a retracted position relative to the outer housing, to a connection-ready state, in which the inner housing is in an extended position relative to the outer housing, wherein the retracted position of the inner housing is closer to the distal end of the outer housing than is the extended position.

2. The cap of claim 1, wherein the proximal end of the outer housing defines a connection interface that is configured to couple with a second cap so as to form a closed assembly.

3. The cap of claim 2, wherein the connection interface is configured to form a fluid-tight seal with the second cap so as to prevent evaporative loss of the antiseptic from the assembly.

4. The cap of claim 2, wherein the connection interface of the inner housing comprises threading.

5. The cap of claim 4, wherein the connection interface defined by the proximal end of the outer housing is devoid of threading.

6. The cap of claim 1, wherein the second biasing member comprises a compression spring.

7. The cap of claim 1, wherein the second biasing member is connected to the inner housing such that the biasing member is configured to inhibit the inner housing from being removed from the outer housing.

8. The cap of claim 7, wherein the second biasing member is in a state of equilibrium when the inner housing is in the extended position.

9. The cap of claim 1, wherein the sealing member is configured to move within the chamber as a male protrusion of a medical connector is inserted into the chamber so as to cause antiseptic to move from one side of the sealing member to another side of the sealing member and into contact with at least a portion of the male protrusion.

10. The cap of claim 1, wherein the first biasing member forces the sealing member into contact with a shelf portion of the inner housing so as to form a seal that prevents evaporative loss of antiseptic from the chamber when the cap is in a pre-use state.

11. The cap of claim 1, wherein the first biasing member comprises a resilient pad that includes at least a portion of the antiseptic therein.

12. The cap of claim 11, wherein the first biasing member further comprises a resilient support member.

13. The cap of claim 1, wherein a proximal end of the inner housing is at an interior of the cavity of the outer housing when the inner housing is in the retracted position, and wherein the proximal end of the inner housing is at an exterior of the outer housing when the inner housing is in the extended position.

14. The cap of claim 1, wherein the inner housing comprises a proximal projection that defines at least a portion of the chamber, and wherein the connection interface of the inner housing comprises threading disposed at an outwardly facing surface of the projection.

15. The cap of claim 1, wherein the outer housing comprises a first movement constraining member and the inner housing comprises a second movement constraining member that is configured to cooperate with the first movement constraining member so as to limit relative movement between the outer and inner housings.

16. The cap of claim 15, wherein the first and second movement constraining members are configured to limit or prevent rotation between the outer and inner housings.

17. The cap of claim 15, wherein the first and second movement constraining members are configured to prevent removal of the inner housing from the outer housing.

18. The cap of claim 15, wherein the first and second movement constraining members are configured to allow a controlled rotation between the outer and inner housings.

19. The cap of claim 15, wherein one of the first and second movement constraining members comprises a spline and the other of the first and second movement constraining members comprises a channel that is sized and shaped to receive the spline therein.

20. The cap of claim 19, wherein each of the spline and the channel defines a helical shape.

21. The cap of claim 1, wherein the outer and inner housings comprise a pair of stopping surfaces that are configured to cooperate with each other to prevent the inner housing from being moved entirely out of the outer housing.

22. The cap of claim 1, further comprising a latching system that is configured to maintain the inner housing in the extended position.

23. The cap of claim 22, wherein one or more of the inner housing and the outer housing comprise at least a portion of the latching system.

24. The cap of claim 22, wherein the second biasing member comprises at least a portion of the latching system.

25. The cap of claim 1, wherein an additional cap is coupled with the cap when the inner housing is in the retracted position, and wherein a connection between the inner housing and the additional cap is configured to move the inner housing from the retracted position to the extended position.

26. The cap of claim 25, wherein the additional cap comprises a connection interface that is configured to couple the additional cap with a medical connector, and wherein the connection interface of the additional cap is coupled with the connection interface of the inner housing when the inner housing is in the retracted position.

27. The cap of claim 25, wherein the connection between the inner housing and the additional cap comprises one or more of a snap fit, a friction fit, and heat stake.

28. The cap of claim 1, wherein the connection interface of the inner housing is configured to complementarily engage a connection interface of a medical connector such that, when the connection interfaces of the inner housing and the medical connector engage each other, the inner housing is drawn into the extended position relative to the outer housing.

29. An assembly configured to disinfect one or more medical connectors, the assembly comprising:
 a female-disinfecting cap that comprises a housing that defines a first connection interface; and
 a male-disinfecting cap that comprises:
  an outer housing that defines a proximal end, a distal end, and a cavity that extends from the proximal end toward the distal end, wherein the outer housing defines a second connection interface that is configured to cooperate with the first connection interface of the female cap to couple the male and female caps with each other;
  an inner housing positioned within the cavity of the outer housing, the inner housing comprising a third connection interface that is configured to connect the inner housing to a medical connector, the inner housing defining a chamber having a sealing member and a first biasing member, wherein the sealing member is configured to form a seal with a portion of a medical connector that is inserted into the chamber, and wherein the first biasing member is configured to urge the sealing member in a proximal direction toward an open end of the chamber; and
  a second biasing member that is coupled with each of the outer and inner housings,
 wherein the second, biasing member is configured to bias the inner housing toward an extended position, wherein, when the assembly is in a pre-use state in which the male and female caps are coupled with each other, a portion of the female cap contacts the inner housing of the male cap so as to maintain the inner housing of the male cap in a retracted position relative to the outer housing of the male cap, and
 wherein the assembly is configured such that upon separation of the male and female-disinfecting caps from each other, the second biasing member is configured to urge the inner housing to the extended position.

30. An assembly configured to disinfect one or more medical connectors, the assembly comprising:
 a female-disinfecting cap that comprises a housing that defines a first connection interface; and
 a male-disinfecting cap that comprises:
  an outer housing that defines a proximal end, a distal end, and a cavity that extends from the proximal end toward the distal end, wherein the outer housing defines a second connection interface that is configured to cooperate with the first connection interface of the female cap to couple the male and female-disinfecting caps with each other to form a closed assembly; and
  an inner housing positioned within the cavity of the outer housing and movable relative thereto and comprising a third connection interface having threading configured to connect the inner houuusing to a medical connector;
 wherein, when the assembly is in a pre-use state in which the male and female disinfecting caps are coupled with each other, the inner housing of the male-disinfecting cap is maintained in a retracted position relative to the outer housing, and wherein the assembly is configured such that during or after separation of the male and female-disinfecting caps from each other, the inner housing of the male-disinfecting cap can be moved to and retained in an extended position relative to the outer housing.

31. A cap configured to disinfect a medical connector, the cap comprising:

an outer housing that defines a proximal end, a distal end, and a cavity that extends from the proximal end toward the distal end;

an inner housing disposed within the outer housing, the inner housing comprising a connection interface that is configured to connect the inner housing to a medical connector, the inner housing defining a chamber having therein an antiseptic, a sealing member and a biasing member, wherein the sealing member is configured to form a seal with a portion of a medical connector that is inserted into the chamber, and wherein the biasing member is configured to urge the sealing member in a proximal direction toward an open end of the chamber; and means for transitioning the inner housing from a retracted position relative to the outer housing to an extended position relative to the outer housing, wherein the retracted position of the inner housing is closer to the distal end of the outer housing than is the extended position.

32. A cap configured to disinfect a medical connector, the cap comprising:

an outer housing that defines a proximal end, a distal end, and a cavity that extends from the proximal end toward the distal end; wherein the outer housing defines a first connection interface to couple with a second cap so as to form a closed assembly; and an inner housing disposed within the outer housing, the inner housing comprising a second connection interface having threading configured to connect the inner housing to a medical connector, the inner housing defining a chamber having an antiseptic therein; and wherein the cap is configured to transition from a pre-use state, in which the inner housing is in a retracted position relative to the outer housing, to a connection-ready state, in which the inner housing is in an extended position relative to the outer housing, wherein the retracted position of the inner housing is closer to the distal end of the outer housing than is the extended position.

33. A cap configured to disinfect a medical connector, the cap comprising:

an outer housing that defines a proximal end, a distal end, and a cavity that extends from the proximal end toward the distal end; and an inner housing disposed within the outer housing, the inner housing comprising a proximal projection defining at least a portion of the chamber and a connection interface having outwardly disposed threading to connect the inner housing to a medical connector, the inner housing defining a chamber having an antiseptic therein; and wherein the cap is configured to transition from a pre-use state, in which the inner housing is in a retracted position relative to the outer housing, to a connection-ready state, in which the inner housing is in an extended position relative to the outer housing, wherein the retracted position of the inner housing is closer to the distal end of the outer housing than is the extended position.

34. An assembly configured to disinfect one or more medical connectors, the assembly comprising:

a female-disinfecting cap that comprises a housing that defines a first connection interface; and a male-disinfecting cap that comprises:

an outer housing that defines a proximal end, a distal end, and a cavity, wherein the outer housing defines a first connection interface that is configured to cooperate with the second connection interface of the female cap to couple the male and female-disinfecting caps with each other to form a closed assembly; and an inner housing disposed within the outer housing, the inner housing comprising a proximal projection defining at least a portion of the chamber, the proximal projection having an outwardly disposed third connection interface having threading to connect the inner housing to a medical connector, the inner housing defining a chamber having an antiseptic therein; and wherein, when the assembly is in a pre-use state in which the male and female disinfecting caps are coupled with each other, the inner housing of the male cap is maintained in a retracted position relative to the outer housing; and wherein the assembly is configured such that during or after separation of the male and female disinfecting caps from each other, the inner housing of the male-disinfecting cap can be moved to and retained in an extended position relative to the outer housing.

\* \* \* \* \*